US007026163B1

(12) United States Patent
Freimuth et al.

(10) Patent No.: US 7,026,163 B1
(45) Date of Patent: Apr. 11, 2006

(54) SULFOTRANSFERASE SEQUENCE VARIANTS

(75) Inventors: Robert R. Freimuth, Rochester, MN (US); Eric D. Wieben, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 440 days.

(21) Appl. No.: 09/792,695

(22) Filed: Feb. 23, 2001

(51) Int. Cl.
C12N 15/11 (2006.01)
C12N 15/54 (2006.01)
C12N 9/10 (2006.01)
C07H 21/04 (2006.01)

(52) U.S. Cl. ............... 435/320.1; 536/23.2; 536/24.31; 435/193

(58) Field of Classification Search ............... 536/23.2, 536/23.5, 23.1, 24.3, 24.31; 435/193, 320.1
See application file for complete search history.

(56) References Cited

U.S. PATENT DOCUMENTS

| 5,451,683 A | 9/1995 | Barrett et al. ............ 548/302.7 |
| 5,733,729 A | 3/1998 | Lipshutz et al. ............... 435/6 |
| 5,770,722 A | 6/1998 | Lockhart et al. .......... 536/25.3 |
| 6,265,561 B1 | 7/2001 | Weinshilboum et al. ... 536/23.2 |

FOREIGN PATENT DOCUMENTS

| WO | WO 98/20019 | 5/1998 |
| WO | WO 99/57318 | 11/1999 |
| WO | WO 99/64630 | 12/1999 |
| WO | WO 00/20605 | 4/2000 |

OTHER PUBLICATIONS

Mehmann et al. (1994) Appl. Environ. Microbiol., vol. 60(9), pp. 3105-3111.*
Mehmann (Sep. 23, 1994) GenBank accession X78089.*
GenBank Accession No. U66036, (Her et al., May 12, 1997).
GenBank Accession No. AF186251, (Freimuth et al., May 31, 2000).
GenBank Accession No. AF186252, (Freimutle et al., May 31, 2000).
GenBank Accession No. AF186253, (Freimutle et al., May 31, 2000).
GenBank Accession No. AF186254, (Freimutle et al., May 31, 2000).
GenBank Accession No. AF186255, (Freimutle et al., May 31, 2000).
GenBank Accession No. AF186256, (Freimutle et al., May 31, 2000).
GenBank Accession No. AF186257, (Freimutle et al., May 31, 2000).
GenBank Accession No. AF186258, (Freimutle et al., May 31, 2000).
GenBank Accession No. AF186259, (Freimutle et al., May 31, 2000).
GenBank Accession No. AF186260, (Freimutle et al., May 31, 2000).
GenBank Accession No. AF186261, (Freimutle et al., May 31, 2000).
GenBank Accession No. AF186262, (Freimutle et al., May 31, 2000).
Campbell et al., "Human Liver Phenol Sulftransferase: Assay Conditions, Biochemical Properties and Partial Purification of Isozymes of the Thermostable Form," *Biochem. Pharmoacol.*, 1987, 36(9):1435-1446.
Cleland, "Computer Programmes for Processing Enzyme Kinetic Data," *Nature*, 1963, 198:463-465.
Freimuth et al., "Pharmacogenetics of Human Sulfotransferase (Sult) IC1:Gene Cloning, Resequencing and Common Single Nucleotide Polymorphisms," *Clinical Pharmacology & Therapeutics*. 2000, 67(2):140.
Cote et al., "Generation of human monoclonal antibodies reactive with cellular antigens," *Proc. Natl. Acad. Sci. USA*, 1983, 80:2026-2030.
Hacia et al., "Detection of heterozygous mutations in *BRCA1* using high density oligonuclcotide arrays and two-color fluorescence analysis," *Nat. Genet.*, 1996, 14:441-447.
Halushka et al., "Patterns of single-nucleotide polymorphisms in candidate genes for blood-pressure homeostasis," *Nat. Genet.*, 1999. 22:239-247.
Her et al., "Human Sulfotransferase SULT1C1: cDNA Cloning, Tissue-Specific Expression. and Chromosomal Localization," *Genomics*, 1997, 41:467-470.
Ho et al., "Site-directed mutagenesis by overlap extension using the polymerase chain reaction," *Gene*. 1989, 77:51-59.
Huse et al., "Generation of a Large Combinatorial Library of the Immunoglobulin Repertoire in Phage Lambda," *Science*, 1989, 246:1275-1281.

(Continued)

Primary Examiner—Elizabeth Slobodyansky
(74) Attorney, Agent, or Firm—Fish & Richardson P.C., P.A.

(57) ABSTRACT

Isolated sulfotransferase nucleic acid molecules that include a nucleotide sequence variant and nucleotides flanking the sequence variant are described, as well as sulfotransferase allozymes. Methods for determining if a mammal is predisposed to thyroid disease or cancer also are described.

5 Claims, 13 Drawing Sheets

OTHER PUBLICATIONS

Hyrup and Nielsen, "Peptide Nucleid Acids (PNA): Synthesis, Properties and Potential Applications," *Bioorgan. Med. Chem.*, 1996, 4:5-23.

Myakishev et al., "High-Throughput SNP Genotyping by Allele-Specific PCR with Universal Energy-Transfer-Labeled Primers," *Genome Res.*, 2001, 11:163-169.

Prince et al., "Robust and Accurate Single Nucleotide Polymorphism Genotyping by Dynamic Allelc-Specific Hybridization (DASH): Design Criteria and Assay Validation," *Genome Res.*, 2001, 11:152-162.

Sakakibara et al., "Molecular Cloning, Expression, and Characterization of Novel Human SULT1C Sulfotransferases That Catalyze the Sulfonation of N-Hydroxy-2-acetylaminofluorene," *J. Biol. Chem.*, 1998, 273 (51):33929-33935.

Schafer and Hawkins, "DNA variation and the future of human genetics." *Nat. Biotechnol.*, 1998, 16:33-39.

Stoneking et al., "Population Variation of Human mtDNA Control Region Sequences Detected by Enzymatic Amplification and Sequence-specific Oligonucleotide Probe," *Am. J. Hum. Genet.*, 1991, 48:370-382.

Summerton and Weller, "Morpholino Antisense Oligomers: Design, Preparation, and Properties." *Antisense & Nucleic Acid Drug Development*, 1997, 7:187-195.

Terwilliger and Ott, *Handbook of Human Genetic Linkage*. The Johns Hopkins University Press, Baltimore and London, 1994, pp. 188-193.

Underhill et al., "Detection of Numurous Y Chromosome Biallelic Polymorphisms by Denaturing High-Performance Liquid Chromatography." *Genome Res.*. 1997. 7 (10):996-1005.

Van Loon et al., "Human Kidney Thiopurine Methyltransferase Photoaffinity Labeling with S-Adenosyl-L-Methionine." *Biochem. Pharmacol.*. 1992, 44(4):775-785.

Van Loon and Weinshilboum, "Thiopurine Methyltransferase Isozymes in Human Renal Tissue," *Drug Metab. Dispos.*, 1990, 18(5):632-638.

Wilkinson, "Statistical Estimations in Enzyme Kinetics," *Biochem, J.*, 1961. 80:324-332.

Wong et al., "Human GM-CSF: Molecular Cloning of the Complementary DNA and Purification of the Natural and Recombinant Proteins," *Science*, 1985, 228:810-815.

Wood et al., "Human Liver Thermolabile Phenol Sulfotransferase: cDNA Cloning, Expression and Characterization," *Biochem. Biophys. Res. Commun.*, 1994, 198(3):1119-1127.

* cited by examiner

```
        TCCAGCCTGGGCAACAGGAGTGAAACACCATCTCAAAAAAAAAAAAAAAAAAGAAAAAAG
1201    ---------+---------+---------+---------+---------+---------+ 1260 (-1115)
        AGGTCGGACCCGTTGTCCTCACTTTGTGGTAGAGTTTTTTTTTTTTTTTTTCTTTTTTC

AAAGAAAAAGAAAGTTCAATTTATTGGGAAAAAAAGAGCCCTTTGGAAACAAGGAGGAAG
1261    ---------+---------+---------+---------+---------+---------+ 1320 (-1055)
        TTTCTTTTTCTTTCAAGTTAAATAACCCTTTTTTCTCGGGAAACCTTTGTTCCTCCTTC

AAGAAGTGTCGGCAAAGAAGCATTAGGAGGTTCAGGGTCAAAGAAGACAAGGAAAGCTTT
1321    ---------+---------+---------+---------+---------+---------+ 1380 (-995)
        TTCTTCACAGCCGTTTCTTCGTAATCCTCCAAGTCCCAGTTTCTTCTGTTCCTTTCGAAA

GGCAAGAAGGGCAGATGGGGTGCAGAATTATGCTTCAATTCCAGAAAGGAAAGCACTGGG
1381    ---------+---------+---------+---------+---------+---------+ 1440 (-935)
        CCGTTCTTCCCGTCTACCCCACGTCTTAATACGAAGTTAAGGTCTTTCCTTTCGTGACCC

GTAGATACAAGGTTGGGGCTGGCAGAAGAGTAGCAGTTCAGAGATCATTAACACTTGATC
1441    ---------+---------+---------+---------+---------+---------+ 1500 (-875)
        CATCTATGTTCCAACCCCGACCGTCTTCTCATCGTCAAGTCTCTAGTAATTGTGAACTAG

5' Flanking
        CATTTAATTTCCCAGGTAACCAAAGACACCATGGAATATAATCTGCCTCCACTAAAGTGT
1501    ---------+---------+---------+---------+---------+---------+ 1560 (-815)
        GTAAATTAAAGGGTCCATTGGTTTCTGTGGTACCTTATATTAGACGGAGGTGATTTCACA
                                                         -760      T→G
        ACCTTTTGTACAATAAGGCAAAGAAAAAATAAGTACACACCTAAGCTCTAGACTTTGTT
1561    ---------+---------+---------+---------+---------+---(---)---+ 1620 (-755)
        TGGAAAACATGTTATTCCGTTTCTTTTTATTCATGTGTGGATTCGAGATCTGAAACAA CTATCCTCTCTGCATTTTCGGTGTGGATGAATACAACTTGGGAAGAAAGGAAAGAAGAAC
1621    ---------+---------+---------+---------+---------+---------+ 1680 (-695)
        GATAGGAGAGACGTAAAAGCCACACCTACTTATGTTGAACCCTTCTTTCCTTTCTTCTTG CAGCAGTTTTAAGCACTTACTATTTGCTCTGCAAAGTGTATTCATCAACATTGTTGCTTT
1681    ---------+---------+---------+---------+---------+---------+ 1740 (-635)
        GTCGTCAAAATTCGTGAATGATAAACGAGACGTTTCACATAAGTAGTTGTAACAACGAAA CAATCTTAAAGCATGGATTGGAGACAGGCAGTATTACCCACACTTCATAGATGCAGAAAT
1741    ---------+---------+---------+---------+---------+---------+ 1800 (-575)
        GTTAGAATTTCGTACCTAACCTCTGTCCGTCATAATGGGTGTGAAGTATCTACGTCTTTA
                         -547      A→G                        -518   C→T
        TAAATCTCAGGCTAAGGAGGAAGGAAAGGGAGTTCACCAAATAAGCAGGAGCCTACCTG
1801    ---------+---------+---(-)---+---------+---------+---(-)---+ 1860 (-515)
        ATTTAGAGTCCGATTCCTCCTTCCTTTCCCTCAAGTGGTTTATTCGTCCTCGGATGGAC
```

FIG. 1A

```
                        -500  T→C
      AAGCCTGATGCATCTGGTCCTAGAGCCAACCTTCCATTTCCCCCCAGCCCCCACCTGTTT       5' Flanking
1861  ----------+----|----+---------+---------+---------+---------+ 1920 (-455)
      TTCGGACTACGTAGACCAGGATCTCGGTTGGAAGGTAAAGGGGGGTCGGGGGTGGACAAA AAGCTTCGAGGCCAGTGGGAGGAGGGAGGGGCCAGGCAGCTGAGGGCCAGGAAAGATGTG
1921  --|-------+---------+---------+---------+---------+---------+ 1980 (-395)
      TTCGAAGCTCCGGTCACCCTCCTCCCTCCCCGGTCCGTCGACTCCCGGTCCTTTCTACAC AAAAACTCTAGCTGGTGACCGAGAGGAGGAGTAGAGTGTGCCCTTAGTTCATATGAACTA
1981  ----------+---------+---------+---------+---------+---------+ 2040 (-335)
      TTTTTGAGATCGACCACTGGCTCTCCTCCTCATCTCACACGGGAATCAAGTATACTTGAT GAGGGAGTTGGTATTTGCACAGCAGTCAGGGTCACATGAGTGATCATGGTACAGTGAGAA
2041  ----------+---------+---------+---------+---------+---------+ 2100 (-275)
      CTCCCTCAACCATAAACGTGTCGTCAGTCCCAGTGTACTCACTAGTACCATGTCACTCTT     Exon 1
                         -258   C→T
      GTTCTCCCTCCCAGGCCAGGTCACAGGGTTTGTTTCTGTTCAATCCGGATTCTTCCAGT
2101  ----------+----|----+---------+---------+---------+---------+ 2160 (-215)
      CAAGAGGGAGGGTCCGGTCCAGTGTCCCAAACAAAGACAAGTTAGGCCTAAGAAGGTCA
                                               -176
      AAAAGCTTCAACTTCCCACACTGAAGCTGAGAGCCTCCCAAAGTGCTGGCTACCTGCTGA
2161  ----------+---------+---------+---------+---------+---------+ 2220 (-155)
      TTTTCGAAGTTGAAGGGTGTGACTTCGACTCTCGGAGGGTTTCACGACCGATGGACGACT
            V    -149            C insertion
      GCGCCCCCGTAACTCTGACACAGTAGTAATTTGAGCCTCTGCAATTGCCGTCTGCTTCCT
2221  ----------+---------+---------+---------+---------+---------+ 2280 (-95)
      CGCGGGGGCATTGAGACTGTGTCATCATTAAACTCGGAGACGTTAACGGCAGACGAAGGA
            Λ
      GTGAAAGTCCTTTCCGTGCCCACTGACCCTTGAGTGGGCCTTTGAGCTGCTGACTTTCAG
2281  ----------+---------+---------+---------+---------+---------+ 2340 (-35)
      CACTTTCAGGAAAGGCACGGGTGACTGGGAACTCACCCGGAAACTCGACGACTGAAAGTC CTGGAACTTGAAGGTAAGAATATGGCTTAAAAGAAATTCTGTACCTAACTCGTTAATTTA
2341  ----------+--|------+---------+---------+---------+|--------+ 2400
      GACCTTGAACTTCCATTCTTATACCGAATTTTCTTTAAGACATGGATTGAGCAATTAAAT
                      I1(37)            T→C
      TTTTTTAACCTTTAGCCACATAGGTGTGGCTTTACAGATGCATTTATTCAAACCAGAAAA
2401  ----------+---------+---------+---------+---------+---------+ 2460
      AAAAAATTGGAAATCGGTGTATCCACACCGAAATGTCTACGTAAATAAGTTTGGTCTTTT     Intron 1

GATCCTAAGAATCTGATAAAATAATATAAAAGAGTTTTGTTAACAGCCTCCAGCCTAAAA
2461  ----------+---------+---------+---------+---------+---------+ 2520
      CTAGGATTCTTAGACTATTTTATTATATTTTCTCAAAACAATTGTCGGAGGTCGGATTTT

ATTCAGACCTAGAAATTCAGGACCCCCCTCAAATCACCTCCAAAAGCTCTCTCTCCTGTA
2521  ----------+---------+---------+---------+---------+---------+ 2580
      TAAGTCTGGATCTTTAAGTCCTGGGGGGAGTTTAGTGGAGGTTTTCGAGAGAGAGGACAT
```

FIG. 1A-1

```
       TTTCCCATAGGGACCCCAACCCTGAGACACTATGGCCCTGACCTCAGACCTGGGGAAACA
361    ---------+---------+---------+---------+---------+---------+ 420 (29)
       AAAGGGTATCCCTGGGGTTGGGACTCTGTGATACCGGGACTGGAGTCTGGACCCCTTTGT
                                                                                Exon 2
       GATAAAACTGAAAGAGGTGGAGGGGACCCTCCTGCAGCCTGCAACTGTGGACAACTGGAG
421    ---------+---------+---------+---------+---------+---------+ 480 (89)
       CTATTTTGACTTTCTCCACCTCCCCTGGGAGGACGTCGGACGTTGACACCTGTTGACCTC CCAGATCCAGAGCTTCGAGGCCAAACCAGATGATCTCCTCATCTGCACCTACCCTAAAGC
481    ---------+---------+---------+---------+---------+---------+ 540 (149)
       GGTCTAGGTCTCGAAGCTCCGGTTTGGTCTACTAGAGGAGTAGACGTGGATGGGATTTCG AGGTGATTGCAGGGTAGGAGGGACAGCAAAGACCTGCTGAGCCAGCACAGGCTCATCACT
541    ---------+---------+---------+---------+---------+---------+ 600
       TCCACTAACGTCCCATCCTCCCTGTCGTTTCTGGACGACTCGGTCGTGTCCGAGTAGTGA TAAGTTAGAATTCCCCTTCTTAGGAAACCTGCTCCTTCTTATTGTTCCACAATGGGTTTT
601    ---------+---------+---------+---------+---------+---------+ 660
       ATTCAATCTTAAGGGGAAGAATCCTTTGGACGAGGAAGAATAACAAGGTGTTACCCAAAA GGAGCTCAGGGCTCACACAGGATGCCTGATATCCGAGTTTTCCAGGAAAGCTGCTATGCT
661    ---------+---------+---------+---------+---------+---------+ 720
       CCTCGAGTCCCGAGTGTGTCCTACGGACTATAGGCTCAAAAGGTCCTTTCGACGATACGA    Intron 2

CTACCATGCACTGGTCTTGGGTGGAGAGACCCTTGCCTGTGCTGCTCCACTCCCTACAGA
721    ---------+---------+---------+---------+---------+---------+ 780
       GATGGTACGTGACCAGAACCCACCTCTCTGGGAACGGACACGACGAGGTGAGGGATGTCT

GATCCAAAGTCCATCCCTCATGGACTTCTATCACTCATGGCAAACAGGATTCTGACCCAA
781    ---------+---------+---------+---------+---------+---------+ 840
       CTAGGTTTCAGGTAGGGAGTACCTGAAGATAGTGAGTACCGTTTGTCCTAAGACTGGGTT

GGGGAGGGTGATGCAAACACCAAGGCTCTACATCCTCTTCGTTTACTCGGGACTCTTCAG
841    ---------+---------+---------+---------+---------+---------+ 900
       CCCCTCCCACTACGTTTGTGGTTCCGAGATGTAGGAGAAGCAAATGAGCCCTGAGAAGTC

GGAAGATTGTCTAACAGATTTCTGCTTCTCATCCTTCCTTTCTGAGCCTCAGGGACAACG
901    ---------+---------+---------+---------+---------+---------+ 960 (159)
       CCTTCTAACAGATTGTCTAAAGACGAAGAGTAGGAAGGAAAGACTCGGAGTCCCTGTTGC
                        179  A→C                                 215    G→A  Exon 3
       TGGATTCAGGAAATTGTGGATATGATTGAACAGAATGGGGACGTGGAGAAGTGCCAGGGA
961    ---------+---------+---------+---------+---------+---------+ 1020 (219)
       ACCTAAGTCCTTTAACACCTATACTAACTTGTCTTACCCCTGCACCTCTTCACGGTCGCT GCCATCATCCAACACCGCCATCCTTTCATTGAGTGGGCTCGGCCACCCCAACCTTCTGGT
1021   ---------+---------+---------+---------+---------+---------+ 1080
       CGGTAGTAGGTTGTGGCGGTAGGAAAGTAACTCACCCGAGCCGGTGGGGTTGGAAGACCA
```

FIG. 1B

```
         GAGAGCACCTCCCTCTTTCTCTCTTCCTGCTTTCTTTCCCTCTCTCTTCTGTTTTCCCCT
1081     ------------+---------+---------+---------+---------+--++ 1140
         CTCTCGTGGAGGGAGAAAGAGAGAAGGACGAAAGAAAGGGAGAGAGAAGACAAAAGGGGA   I3(61-62)
                                                                       CT
         GTCTTTTCTCACTTTTCTCCTCTTCTCTCCTCTCTCTCCCCCATCTCTCCTTCCTCTT    deletion
1141     ------------+---------+---------+---------+----+----+------+ 1200
         CAGAAAAGAGTGAAAAGAGGAGAAGAGAGGAGAGAGAGAGGGGGTAGAGAGGAAGGAGAA
                                                     I3(107)       30 nucleotide
                                                                   deletion
         TTCTCTCTCCCTCCCTCTCTCCTTCCTCTTCTCTTTCTCTCTCATTTTCACTGTCATATG
1201     ----------+----+----+---------+---------+---------+---------+ 1260
         AAGAGAGAGGGAGGGAGAGAGGAAGGAGAAGAGAAAGAGAGAGTAAAAGTGACAGTATAC TTTCTTCCTTTTATCTTCCTCTCATCCTCTGTCTACATATTATTTAAGATTTTTTACCAA
1261     ------------+---------+---------+---------+---------+---------+ 1320
         AAAGAAGGAAAATAGAAGGAGAGTAGGAGACAGATGTATAATAAATTCTAAAAAATGGTT AAGTGAATCACCAAATGAAAAGGATGTGTGCTAGGGTCAGATTCTGCCTTATTTTCTTCT
1321     ------------+---------+---------+---------+---------+---------+ 1380
         TTCACTTAGTGGTTTACTTTTCCTACACACGATCCCAGTCTAAGACGGAATAAAAGAAGA TAAGCCCTCCCTCTGATCATGTGCAACTGTAGATCACATTGAAGATGTGAAAAACTGTAA
1381     ------------+---------+---------+---------+---------+---------+ 1440
         ATTCGGGAGGGAGACTAGTACACGTTGACATCTAGTGTAACTTCTACACTTTTTGACATT

GCCATTT
1441     ------- 1447
         CGGTAAA
```

FIG. 1B-1

```
        TGTTTTCAACTTTCTCTTTTATTCCTTTGCACTTTTTTTTGAGACAGGGTCTCACTCTGT
481 ----------+----------+----------+----------+----------+----------+ 540
        ACAAAAGTTGAAAGAGAAAATAAGGAAACGTGAAAAAAAACTCTGTCCCAGAGTGAGACA

Intron 3
        CACCCAGGCTAGAGTGCAGTAGTGCAAACACAGCTCACTGCAGCCTCAATTCT CTCGAGC
541 ----------+----------+----------+----------+----------+---┼------+ 600
        GTGGGTCCGATCTCACGTCATCACGTTTGTGTCGAGTGACGTCGGAGTTAAGA GAGCTCG
                                                                  I3(-2377)   T insertion
        TCAAGCGATCCTCCCATCTCAGCCTCCCGAGTAAGTAGCTGGGACTACAGGTGCGTATCA
601 ----------+----------+----------+----------+----------+----------+ 660
        AGTTCGCTAGGAGGGTAGAGTCGGAGGGCTCATTCATCGACCCTGATGTCCACGCATAGT CCATGCCCAGCTAATTTTGGTATTTTTTTTTTTAGAGACAGGATTTCACCATGTTGCCC
661 ----------+----------+----------+------┼---+----------+----------+ 720
        GGTACGGGTCGATTAAAACCATAAAAAAAAAAAATC TCTGTCCTAAAGTGGTACAACGGG
                                                                              Exon 3b
        AGGCTGGTCTCAAACTCCTGAGCTCAAGCAATCCACCTGCCTCAACCTCCCAAAGTGCCA
721 ----------+----------+----------+----------+----------+----------+ 780
        TCCGACCAGAGTTTGAGGACTCGAGTTCGTTAGGTGGACGGAGTTGGAGGGTTTCACGGT AGATTACAGA C GTGAGCCACTGCCCCTGG C TTCTTTGCATATTTTAAACATAGTTATTT
781 ----------+-┼--------+----------+--┼-------+----------+----------+ 840
        TCTAATGTCT G CACTCGGTGACGGGGAC C G GAAGAAACGTATAAAATTTGTATCAATAAA
                     I3(-2177)  C→T    I3(-2118)  I3(-2158)  C→T
        ATATTCTCTATTAGGTACCCAATAACTGAGGTCACTAGGGGTTTAGTTCTTCCACCTGTT
841 ----------+----------+----------+----------+----------+----------+ 900
        TATAAGAGATAATCCATGGGTTATTGACTCCAGTGATCCCCAAATCAAGAAGGTGGACAA
              I3(-2227)

TTTTTTCTAGCTCTTGTTCATAGGGCTTTTCCCTCATTTGTTTTGTAATTTTGTATAAAA
901 ----------+----------+----------+----------+----------+----------+ 960
        AAAAAAGATCGAGAACAAGTATCCCGAAAAGGGAGTAAACAAAACATTAAAACATATTTT
                                                                              Intron 3
        AGCTCTTTTCTCCCTGTCTTGATCTCACACCTACATTGGAACATTTCCAATCTAGAATAG
961 ----------+----------+----------+----------+----------+----------+ 1020
        TCGAGAAAAGAGGGACAGAACTAGAGTGTGGATGTAACCTTGTAAAGGTTAGATCTTATC TTTAAGTTAACTTCTGGTCCAAGCTGGTAGTATAATTTCATATCCATGCATGTAGTATGA
1021----------+----------+----------+----------+----------+----------+ 1080
        AAATTCAATTGAAGACCAGGTTCGACCATCATATTAAAGTATAGGTACGTACATCATACT AAACAGGATTGTGGTTATGAGTTCTCAAGAAAGCCTCTTTTTCTGCACCCAGAGGCGAGG
1081----------+----------+----------+----------+----------+----------+ 1140
        TTTGTCCTAACACCAATACTCAAGAGTTCTTTCGGAGAAAAAGACGTGGGTCTCCGCTCC

CAAGGAA
1141-------  1147
        GTTCCTT
```

FIG. 1C

```
      TGCTGCAGGCACATGGGGGTCATCTCTGGCTGGCAGGAAGGTGAGGGAGTCCTCTCTTCT
  1   ---------+---------+---------+---------+---------+---------+ 60
      ACGACGTCCGTGTACCCCCAGTAGAGACCGACCGTCCTTCCACTCCCTCAGGAGAGAAGA

CTGGTCCTGGCTGACTCTGCCTCAGCAGGACTTCACTTGACCATTCTCACCTTCTGTCAC
 61   ---------+---------+---------+---------+---------+---------+ 120
      GACCAGGACCGACTGAGACGGAGTCGTCCTGAAGTGAACTGGTAAGAGTGGAAGACAGTG
                                                                    Intron 3
      CTCATCCTTAAAGTGACAGAGTAAATTAACTCTAAGGCCCCATCCAGGACTCAAGCTGTG
121   ---------+---------+---------+---------+---------+---------+ 180
      GAGTAGGAATTTCACTGTCTCATTTAATTGAGATTCCGGGGTAGGTCCTGAGTTCGACAC TGATTTTACAAAAATGAAAATTATATTAATAATCCCATTGTAAAATCCCAAAAGAAAGTC
181   ---------+---------+---------+---------+---------+---------+ 240
      ACTAAAATGTTTTTACTTTTAATATAATTATTAGGGTAACATTTTAGGGTTTTCTTTCAG
                                                    I3(-80)   G→A
      AAGAGACTAGCAGAAAGACAGGTGGGTGATGGGATGTCCTGGACAGAGCCTGGATCATGA
241   ---------+---------+---------+--------+---------+---------+ 300
      TTCTCTGATCGTCTTTCTGTCCACCCACTACCCTACGGACCTGTCTCGGACCTAGTACT GGTCCCCATGTAGTGCTTGTACTACGCAGATGTTTCCTCTTGAGCTATTTTAAAGTGTG
301   ---------+---------+---------+---------+---------+---------+ 360(282)
      CCAGGGGTACATCACGAACATGATGCGTCTACAAAGGAGAACTCGATAAAATTTCACAC
                                                                    Exon 4
      GAAAAAGCCAAAGCAATGCCCTCTCCACGGATACTAAAGACTCACCTTTCCACTCAGCTG
361   ---------+---------+---------+---------+--------+---------+ 420(342)
      CTTTTTCGGTTTCGTTACGGGAGAGGTGCCTATGATTTCTGAGTGGAAAGGTGAGTCGAC
                                                        332   Exon 3B
                                                        C→T   Splices in here
```

FIG. 1D

```
    CTGCCACCGTCTTTCTGGGAAAACAACTGCAAGGTAAGATACCAACAGCTCCCTGTGACA
421 ------------+---------+---------+---+-----+---------+---------+ 480
    GACGGTGGCAGAAAGACCCTTTTGTTGACGTTCCATTCTATGGTTGTCGAGGGACACTGT
                                              I4(68)    C→A
    GAAGGGAAAGTAAGCCAACCAAAGCGAGTCCTGCAGACCCCAACGCAGAGCATTCGTGAT
481 ---------+---------+---------+---------+-+-------+---------+ 540
    CTTCCCTTTCATTCGGTTGGTTTCGCTCAGGACGTCTGGGGTTGCGTCTCGTAAGCACTA
         I4(94)     T→C
    CACCTTTGCCTCTCCACTGTCTCTGATGCTTACCAGCAAAGAGAAAACATAAAGTTCTAC
541 -----+-+---------+---------+---------+---------+---------+ 600
    GTGGAAACGGAGAGGTGACAGAGACTACGAATGGTCGTTTCTCTTTTGTATTTCAAGATG
                                                                Intron 4
    ATTCAGCAGGACATTCACCTGAACAGTTTCAAATAGGACATGAAGGCAGGATCCAGATTG
601 ---------+---------+---------+---------+---------+---------+ 660
    TAAGTCGTCCTGTAAGTGGACTTGTCAAAGTTTATCCTGTACTTCCGTCCTAGGTCTAAC AATGTTTGGAGGGAACTAGAGACATGGGGAGGCAGTGAGTGCAGTAAGCGTAGCTGTGAA
661 ---------+---------+---------+---------+---------+---------+ 720
    TTACAAACCTCCCTTGATCTCTGTACCCCTCCGTCACTCACGTCATTCGCATCGACACTT ATGAAGGGGAGAAGATGGTGGTCCCAGGCTGCAGGCCATGGGGAGGTTTTCTAACAGACC
721 ---------+---------+---   ----+---------+---------+---------+ 780
    TACTTCCCCTCTTCTACCACCAGGGTCCGACGTCCGGTACCCCTCCAAAAGATTGTCTGG

AGGGAGGGAAGAATGAGAG
781 ---------+---------
    TCCCTCCCTTCTTACTCTC
```

FIG. 1D-1

```
                                        I4(-20)    C→T
     AAGTCCACTTTTTATACCATCTTTTACCCACCTCTTTTCTTACCCCAAAGTTCCTTTATG
301  ---------+---------+---------+-|-------+---------+|--------+ 360 (385)
     TTCAGGTGAAAAATATGGTAGAAAATGGGTGGAGAAAAGAATGGGGTTTCAAGGAAATAC
                                                                   Exon 5
     TAGCTCGAAATGCCAAAGACTGTATGGTTTCCTACTACCATTTCCAAAGGATGAACCACA
361  ---------+---------+---------+---------+---------+---------+ 420
     ATCGAGCTTTACGGTTTCTGACATACCAAAGGATGATGGTAAAGGTTTCCTACTTGGTGT TGCTTCCTGACCCTGGTACCTGGGAAGAGTATTTTGAAACCTTCATCAATGGAAAAGTA
421  ---------+---------+---------+---------+---------+------+--+ 480
     ACGAAGGACTGGGACCATGGACCCTTCTCATAAAACTTTGGAAGTAGTTACCTTTTCCAT CGGGAACATCCTTCACACCCTTGCATTCTCACTCCAGCTAGGCTGGGTCTAGGGAACCAC
481  ---------+---------+---------+---------+---------+---------+ 540
     GCCCTTGTAGGAAGTGTGGGAACGTAAGAGTGAGGTCGATCCGACCCAGATCCCTTGGTG
                                        I5(97)   T→A
     AGGCAGCATTTTATCCCCTAGAATGCCTGTACTTCATCAGGTGTGTCCTACCACAGACTG
541  ---------+---------+---------+--|-|----+---------+---------+ 600
     TCCGTCGTAAAATAGGGGATCTTACGGACATGAAGTAGTCCACACAGGATGGTGTCTGAC GGACTGGGCAGAGCAAGCTGGCCACTGAGTGTATGCCCACAGCCCTCAGCAAACATCTTC
601  ---------+---------+---------+---------+---------+---------+ 660
     CCTGACCCGTCTCGTTCGACCGGTGACTCACATACGGGTGTCGGGAGTCGTTTGTAGAAG
                                                                   Intron 5
     CACCTGATTCAGAGTCTTTAATTACAGCCATCCTCTTCCAAAAGGTGTCCTTGTCCCTAT
661  ---------+---------+---------+---------+---------+---------+ 720
     GTGGACTAAGTCTCAGAAATTAATGTCGGTAGGAGAAGGTTTTCCACAGGAACAGGGATA GTGATTGCACATAATAGGAAGCCACTTTAGGGACGATGTTGGGGCAAGTAACCCTAAGGC
721  ---------+---------+---------+---------+---------+---------+ 780
     CACTAACGTGTATTATCCTTCGGTGAAATCCCTGCTACAACCCCGTTCATTGGGATTCCG TGTCCCCATCTACACCACCCTCAAAATCAAACAGATCAGAACCCTTAGGACATATCTAAT
781  ---------+---------+---------+---------+---------+---------+ 840
     ACAGGGGTAGATGTGGTGGGAGTTTTAGTTTGTCTAGTCTTGGGAATCCTGTATAGATTA ACAGAATTTGGGTTTTCTCTCTAACTCACTTCAGGAAAATCCCTAATACTCAGAAGGT
841  ---------+---------+---------+---------+---------+---------+ 900
     TGTCTTAAACCCAAAAGAGAGAGATTGAGTGAAGTCCTTTTAGGGATTATGAGTCTTCCA TTTGTGTGATGCCTATGTAGACTATTCTGTTTCCTGTGTCTATTTCAGTGGTTTGGGGTT
901  ---------+---------+---------+---------+--------+|---------+ 960 (514)
     AAACACACTACGGATACATCTGATAAGACAAAGGACACAGATAAAGTCACCAAACCCCAA
                                                                   Exon 6
     CCTGGTTTGACCACGTGAAAGGATGGTGGGAGATGAAAGACAGACACCAGATTCTCTTCC
961  ---------+---------+---------+---------+---------+---------+ 1020 (574)
     GGACCAAACTGGTGCACTTTCCTACCACCCTCTACTTTCTGTCTGTGGTCTAAGAGAAGG
```

FIG. 1E

```
                577      T→C
     T C T T C T A T G A G G A C A T A A A G A G G G T G A G T G A A G G C T C T G C A G A A G A A C C A T T T T A A A G T G
1021 ---------+---------+---------+---------+---------+---------+ 1080
     A G A A G A T A C T C C T G T A T T T C T C C C A C T C A C T T C C G A G A C G T C T T C T T G G T A A A A T T T C A C
                                                  I6(73)    A→G                                                    Intron 6

G T T C T T C A G G T G C A G A G A A A T T C A A A G T T G T T T C A A G G A C A T C C C A G A G A A T T G T A G T A
1081 ---------+---------+---------+---------+---------+---------+ 1140
     C A A G A A G T C C A C G T C T C T T T A A G T T T C A A C A A A G T T C C T G T A G G G T C T C T T A A C A T C A T

T T T C T T T A T G A T A C T C T C A T T C A T T C C A G T C C A A T G T T A C C C T T G C C G C A G G A C C C A A A G
1141 ---------+---------+---------+---------+---------+---------+ 1200 (606)
     A A A G A A A T A C T A T G A G A G T A A G T A A G G T C A G G T T A C A A T G G G A A C G G C G T C C T G G G T T T C
                                                                                              599
                                                                                              A→T
     C A T G A A A T T C G G A A G G T G A T G C A G T T C A T G G G A A A G A A G G T G G A T G A A A C A G T G C T A G A T
1201 ---------+---------+---------+---------+---------+---------+ 1260 (666)
     G T A C T T T A A G C C T T C C A C T A C G T C A A G T A C C C T T T C T T C C A C C T A C T T T G T C A C G A T C T A    Exon 7

715  A→G
     A A A A T T G T C C A G G A G A C G T C A T T T G A G A A A A T G A A A G A A A A T C C C A T G A C A A A T C G T T C T
1261 ---------+---------+---------+---------+---------+---------+ 1320 (726)
     T T T T A A C A G G T C C T C T G C A G T A A A C T C T T T T A C T T T C T T T T A G G G T A C T G T T T A G C A A G A
                                                  763 T→G
     A C A G T T T C C A A A T C T A T C T T G G A C C A G T C A A T T T C C T C C T T C A T G A G A A A A G G T G T G T G G
1321 ---------+---------+---------+---------+---------+---------+ 1380
     T G T C A A A G G T T T A G A T A G A A C C T G G T C A G T T A A A G G A G G A A G T A C T C T T T T C C A C A C A C C

G G C C T C T T T A T C A T A C A T T C A G A T T G T C T C G T A A C A T C C T G T C T G C C T C T T A G C A G A C A A
1381 ---------+---------+---------+---------+---------+---------+ 1440
     C C G G A G A A A T A G T A T G T A A G T C T A A C A G A G C A T T G T A G G A C A G A C G G A G A A T C G T C T G T T

T A T T G A G T T T T A T T A A T T C C A A G C C A A T G C A T T T C A A C T A T T C C T A A T A T G T G T T T C T A A
1441 ---------+---------+---------+---------+---------+---------+ 1500
     A T A A C T C A A A A T A A T T A A G G T T C G G T T A C G T A A A G T T G A T A A G G A T T A T A C A C A A A G A T T    Intron 7

```
    TTGCTCAACATAATGTTTTGAGATTCCTCCATGTGGTTGTGTGTCTGTAGTTCATCATTC
  1 ---------+---------+---------+---------+---------+---------+ 60
    AACGAGTTGTATTACAAAACTCTAAGGAGGTACACCAACACACAGACATCAAGTAGTAAG

TTTTATGTCTATGTAGTAATCCATCAGGTAAATACACTACAGGTGGGGCCAGGTCATGCA
 61 ---------+---------+---------+---------+---------+---------+ 120
    AAAATACAGATACATCATTAGGTAGTCCATTTATGTGATGTCCACCCCGGTCCAGTACGT

GGCCACTAGCTGCCTTGGGTCAGTTGTCCAGCTGACTTAGAAGTCCATCCCCCTGCACAG
121 ---------+---------+---------+---------+---------+---------+ 180
    CCGGTGATCGACGGAACCCAGTCAACAGGTCGACTGAATCTTCAGGTAGGGGACGTGTC
                                                          Intron 7
    AGTCCCCTAGGCCTGCTTCTTATAGGAGAGCTGCTCATGGACAGGTGTCCACTGAAGGGG
181 ---------+---------+---------+---------+---------+---------+ 240
    TCAGGGGATCCGGACGAAGAATATCCTCTCGACGAGTACCTGTCCACAGGTGACTTCCCC
                                ↓ I7(-101)    A insertion
    GAGTTGGGTGAGTCAGGTATGTGGACAGGCCAGATTCAGTATGGGCACTACACCACTTTA
241 ---------+--------+---------+---------+---------+---------+ 300
    CTCAACCCACTCAGTCCATACACCTGTCCGGTCTAAGTCATACCCGTGATGTGGTGAAAT
                         ↑
    CTCAGGGACACCACATCTTTCAATCAGAGTGACACTCCTGTCTGGCCTTCCTTTTTCTAG
301 ---------+---------+---------+---------+---------+---------+ 360
    GAGTCCCTGTGGTGTAGAAAGTTAGTCTCACTGTGAGGACAGACCGGAAGGAAAAAGATC
```

FIG. 1F

```
             GAACTGTGGGGGATTGGAAAAACCACTTCACTGTTGCCCAGAATGAGAGGTTTGATGAAA
(779) 361   ------------+----------+----------+----------+----------+----------+ 420 (838)
             CTTGACACCCCCTAACCTTTTTGGTGAAGTGACAACGGGTCTTACTCTCCAAACTACTTT

TCTATAGAAGAAAGATGGAAGGAACCTCCATAAACTTCTGCATGGAACTCTGAGCAAGAT
      421   ------------+----------+----------+----------+----------+----------+ 480 (898)
             AGATATCTTCTTTCTACCTTCCTTGGAGGTATTTGAAGACGTACCTTGAGACTCGTTCTA

GTAAATAAAATTAAAAGGTGGATGGCAAGAGTGCAAATACTATCTTCAATCCTTCAGTCC
      481   ------------+----------+----------+----------+----------+----------+ 540 (958)
             CATTTATTTTAATTTTCCACCTACCGTTCTCACGTTTATGATAGAAGTTAGGAAGTCAGG
                                                                              Exon 8

CAGCCAGAAGAATCTCTGAAAGCATATTGTGAATGTATACAATGTAGTACAAACAATCTC
      541   ------------+----------+----------+----------+----------+----------+ 600 (1018)
             GTCGGTCTTCTTAGAGACTTTCGTATAACACTTACATATGTTACATCATGTTTGTTAGAG

TGTGATGATTAACAGTATGTCACCACTTCATTTTTAAAAAGGATCACGTCTAATGCCCA
      601   ------------+----------+----------+----------+----------+----------+ 660 (1078)
             ACACTACTAATTGTCATACAGTGGTGAAGTAAAAAATTTTTCCTAGTGCAGATTACGGGT
                        1027   T→C

TTTTCCCAACTATTCTTTCCAAAGTAAGATATAAGGTAGCTTAATAAACTAAGTAAAACG
      661   ------------+----------+----------+----------+----------+----------+ 720 (1138)
             AAAAGGGTTGATAAGAAAGGTTTCATTCTATATTCCATCGAATTATTTGATTCATTTTGC

TATGACTTGAGTACAAAAGGATTGTTTTAATCCCCATTATTCTGGAAAGTGCATCCTAGT
      721   ------------+----------+----------+----------+----------+----------+ 780 (1198)
             ATACTGAACTCATGTTTTCCTAACAAAATTAGGGGTAATAAGACCTTTCACGTAGGATCA
                                                                  1191  A→G

CTCCCAGTCTATAACATCATAATACCTTGAGTATAAGTCCAAATATTAGGTTATATCTAT
      781   ------------+----------+----------+----------+----------+----------+ 840 (1258)
             GAGGGTCAGATATTGTACTATTATGAACTCATATTCAGGTTTATAATCCAATATAGATA
             1260  T→C            1217  A→G                      1251  A→G

ATTAAAAACAAAATTTCTGTCATCTGTCCTGGCCATTCAGGCAACTCCAGCCTGGGCTCA
      841   ------------+----------+----------+----------+----------+----------+ 900 (1318)
             TAATTTTTGTTTTAAAGACAGTAGACAGGACCGGTAAGTCCGTTGAGGTCGGACCCGAGT
                                                                          3' Flanking ATCCTGGAGTTCTGTCTGGTCACTATCAGAAGGAACACTTTGAGGGAAACCCTGGTGCAG
      901   ------------+----------+----------+----------+----------+----------+ 960 (1378)
             TAGGACCTCAAGACAGACCAGTGATAGTCTTCCTTGTGAAACTCCCTTTGGGACCACGTC CCAGCCCTGAGGAAACATGGCCTGAGTGCCCTCACTGGTGGGTGGGAATAAAATGGAAGT
      961   ------------+----------+----------+----------+----------+----------+ 1020 (1438)
             GGTCGGGACTCCTTTGTACCGGACTCACGGGAGTGACCACCCACCCTTATTTTACCTTCA GCACAGAGGAGATGTCAGAAGACCAAAACTTGGTGAATAGTCCCAGTGCTAGGTCATATA
     1021   ------------+----------+----------+----------+----------+----------+ 1080 (1498)
             CGTGTCTCCTCTACAGTCTTCTGGTTTTGAACCACTTATCAGGGTCACGATCCAGTATAT
```

FIG. 1F-1

```
atgccctga cctcagacct ggggaaacag ataaaactga aagaggtgga gggaccctc
ctgcagcctg caactgtgga caactggagc cagatccaga gcttcgaggc caaaccagat
gatctcctca tctgcaccta ccctaaagca gggacaacgt ggattcagga aattgtggat
atggtgaac agaatgggga cgtggagaag tgccagcgag ccatcatcca acaccgccat
cctttcattg agtgggctcg gccacccca cctttctggtg tgaaaaagc caaagcaatg
ccctctccac ggatactaaa gactcacctt tccactcagc tgctgccacc gtctttctgg
gaaacaact gcaagttcct ttatgtagct cgaaatgcca aagactgtat ggtttcctac
taccatttcc aaaggatgaa ccacatgctt cctgacccctg gtacctggga agagtatttt
gaaccttca tcaatggaaa agtggttttgg ggttcctggt ttgaccacgt gaaggatgg
tgggagatga agacagaca ccagattctc ttcctcttct atgaggacat aaagagggac
ccaagcatg aaattcggaa ggtgatgcag gacgtcattt tgaccgcct atgaggaa agaaaatcc catgacaaat
ctagataaaa ttgtccagga gacgtcattt tatcttggac cctccttcat gagaaaagga
cgttctacag tttccaaatc tatcttggac cagtcaattt gttgccaga atgagaggtt tgatgaaatc
actgtgggg attgaaaaa ccacttcact aacctccata aacttctgca tggaactctg a
```

FIG. 2A

MALTSDLGKQIKLKEVEGTLLQPATVDNWSQIQSFEAKPDDLLICTYPKAGTTWIQEIVDMIEQNGD
VEKCQRAIIQHRHPFIEWARPPQPSGVEKAKAMPSPRILKTHLSTQLLPPSFWENNCKFLYVARNA
KDCMVSYYHFQRMNHMLPDPGTWEEYFETFINGKVVWGSWFDHVKGWWEMKDRHQILFLFYE
DIKRDPKHEIRKVMQFMGKKVDETVLDKIVQETSFEKMKENPMTNRSTVSKSILDQSISSFMRKGT
VGDWKNHFTVAQNER FDEIYRRKMEGTSINFCMEL

SULFOTRANSFERASE SEQUENCE VARIANTS

STATEMENT AS TO FEDERALLY SPONSORED RESEARCH

Funding for the work described herein was provided in part by the federal government, which may have certain rights in the invention.

TECHNICAL FIELD

The invention relates to sulfotransferase nucleic acid and amino acid sequence variants.

BACKGROUND

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which, in mammals, is divided into two families, SULT1 or phenol SULTs and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) subfamilies. SULT2 subfamilies include two hydroxysteroid SULTs, 2A1 and 2B1.

Members of the SULT1C subfamily, including SULT1C1 and SULT1C2, catalyze the sulfate conjugation of thyroid hormones and carcinogenic hydroxyarylamines. A human SULT1C1 cDNA, which was cloned from a fetal liver-spleen cDNA library, encodes a protein that is 62% identical to the amino acid sequence of a rat SULT designated "ST1C1". Her et al., *Genomics* (1997) 41: 467–470. ST1C1 catalyzes the metabolic activation of the procarcinogen N-hydroxy-2-acetylaminofluorene. The amino acid sequences of human SULT1C1 and human SULT1C2 are 62.6% identical. Sakakibara et al., *J. Biol. Chem.* (1998) 273:33929–33935. Human SULT1C1 is highly expressed in stomach, kidney, liver, and thyroid, while SULT1C2 is highly expressed in fetal lung and fetal kidney.

SUMMARY

The invention is based on the discovery of sequence variants that occur in both coding and non-coding regions of SULT1C1 nucleic acids. Certain SULT1C1 nucleotide sequence variants encode SULT1C1 enzymes that are associated with individual differences in enzymatic activity. Other SULT1C1 sequence variants in non-coding regions of the SULT1C1 nucleic acid may alter regulation of transcription and/or splicing of the SULT1C1 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of SULT1C1 sequence variants also allows predisposition to hormone dependent diseases or chemical carcinogenesis to be assessed in individuals.

In one aspect, the invention features an isolated nucleic acid molecule that includes a SULT1C1 nucleic acid sequence, wherein the nucleic acid molecule is at least ten nucleotides in length, and wherein the SULT1C1 nucleic acid sequence includes a nucleotide sequence variant. The nucleotide sequence variant can be within a coding sequence, an intron sequence, a 5' untranslated sequence, or a 3' untranslated sequence, and can be a nucleotide deletion, a nucleotide insertion, or a nucleotide substitution. The nucleotide sequence variant can be at one or more positions selected from the group consisting of 179, 218, 332, 577, 599, 715, and 763 relative to the adenine of the SULT1C1 translation initiation codon, e.g., at one or more positions selected from the group consisting of a cytosine substitution for adenine at position 179, an adenine substitution for guanine at position 218, a thymine substitution for cytosine at position 332, a cytosine substitution for thymine at position 577, a thymine substitution for adenine at position 599, a guanine substitution for adenine at position 715, and a guanine substitution for thymine at position 763.

The nucleotide sequence variant can be at position 37 relative to the guanine in the splice donor site of intron 1, e.g., a cytosine substitution for thymine. The nucleotide sequence variant can be at position 61 or 62 relative to the guanine in the splice donor site of intron 3, e.g., a variant selected from the group consisting of a cytosine deletion at position 61, a thymine deletion at position 62, and a cytosine and thymine deletion at positions 61 and 62, respectively. The nucleotide sequence variant is at position 107 relative to the guanine in the splice donor site of intron 3. The nucleotide sequence variant can be a deletion comprising the nucleotide sequence of 5'-TCTCTCCTTC-CTCTTTTCTCTCTCCCTCCC-3' (SEQ ID NO:3). The nucleotide sequence variant can be at one or more positions selected from the group consisting of −80, −2158, −2177, and −2377 relative to the guanine in the splice acceptor site of intron 3, e.g., at one or more positions selected from the group consisting of an adenine substitution for guanine at position −80, a thymine substitution for cytosine at position −2158, a thymine substitution for cytosine at position −2177, and a thymine insertion at position −237.

The nucleotide sequence variant can be at position 68 or 94 relative to the guanine in the splice donor site of intron 4, e.g., selected from the group consisting of an adenine substitution for cytosine at position 68 and a cytosine insertion for thymine at position 94. The nucleotide sequence variant can be at position −20 relative to the guanine in the splice acceptor site of intron 4, e.g., a thymine substitution for cytosine. The nucleotide sequence variant can be at position 97 relative to the guanine in the splice donor site of intron 5, e.g., an adenine substitution for thymine. The nucleotide sequence variant can be at position 73 relative to the guanine in the splice donor site of intron 6, e.g., a guanine substitution for adenine. The nucleotide sequence variant can be at position −101 relative to the guanine in the splice acceptor site of intron 7, e.g., an adenine insertion. The nucleotide sequence variant can be at one or more positions selected from the group consisting of −149, −258, −500, −518, −547, and −760 relative to the adenine of the SULT1C1 translation initiation codon, e.g., at one or more positions selected from the group consisting of a cytosine insertion at position −149, a thymine substitution for cytosine at position −258, a cytosine substitution for thymine at position −500, a thymine substitution for cytosine at position −518, a guanine substitution for adenine at position −547, and a guanine substitution for thymine at position −760.

The nucleotide sequence variant can be at one or more positions selected from the group consisting of 1027, 1191, 1217, 1251, or 1260 relative to the adenine of the SULT1C1 translation initiation codon, e.g., at one or more positions selected from the group consisting of a cytosine substitution for thymine at position 1027, a guanine substitution for adenine at position 1191, a guanine substitution for adenine at position 1217, a guanine substitution for adenine at position 1251, and a cytosine substitution for thymine at position 1260.

The invention also features an isolated nucleic acid encoding a SULT1C1 polypeptide, wherein the polypeptide includes a SULT1C1 amino acid sequence variant. The amino acid sequence variant can be at one or more residues selected from the group consisting of 60, 73, 111, 193, 200, 239, and 255.

In another aspect, the invention features an isolated SULT1C1 polypeptide, wherein the polypeptide includes a SULT1C1 amino acid sequence variant. The polypeptide can include a SULT1C1 amino acid sequence variant at one or more residues selected from the group consisting of 60, 73, 111, 193, 200, 239, and 255. For example, the amino acid sequence variant at residue 60 can be an alanine; the amino acid sequence variant at residue 73 can be a glutamine; the amino acid sequence variant at residue 111 can be a phenylalanine; the amino acid sequence variant at residue 193 can be a leucine; the amino acid sequence variant at residue 200 can be a valine; the amino acid sequence variant at residue 239 can be an alanine; or the amino acid sequence variant at residue 255 can be an alanine. The amino acid sequence variant can be at residues 200 and 239, 60 and 255, or 73 and 255. Activity of the polypeptide can be altered relative to a wild type SULT1C1 polypeptide.

In yet another aspect, the invention features an article of manufacture that includes a substrate, wherein the substrate includes a population of isolated SULT1C1 nucleic acid molecules, each nucleic acid molecule including a SULT1C1 nucleotide sequence variant. The substrate can include a plurality of discrete regions, wherein each region includes a different population of isolated SULT1C1 nucleic acid molecules, and wherein each population of molecules includes a different SULT1C1 nucleotide sequence variant.

The invention also features a method for determining if a mammal is predisposed to a thyroid disease. The method includes obtaining a biological sample from the mammal, and detecting the presence or absence of a SULT1C1 nucleotide sequence variant in the sample, wherein predisposition to a thyroid disease is determined based on the presence or absence of the variant. The method further can include detecting the presence or absence of a plurality of the SULT1C1 nucleotide sequence variants in the sample to obtain a variant profile of the mammal, and wherein predisposition to a thyroid disease is determined based on the variant profile.

In another aspect, the invention features a method for determining if a mammal is predisposed to cancer. The method includes obtaining a biological sample from the mammal, and detecting the presence or absence of a SULT1C1 nucleotide sequence variant in the sample, wherein predisposition to cancer is determined based on the presence or absence of the variant. The method further can include detecting the presence or absence of a plurality of the SULT1C1 nucleotide sequence variants in the sample to obtain a variant profile of the mammal, and wherein predisposition to cancer is determined based on the variant profile. The cancer can be a chemically induced cancer.

The invention also features a method for obtaining a SULT1C1 variant profile. The method includes obtaining a biological sample from a mammal, and detecting the presence or absence of a plurality of SULT1C1 nucleotide sequence variants in the sample to obtain a variant profile of the mammal. The method further can include communicating the profile to a medical or research professional.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A–1F are the nucleotide sequence of the reference SULT1C1. Single nucleotide polymorphisms (SNPs) are circled, insertions are indicated with a line, and deletions are indicated by two lines that bound the deleted sequence. The position and nature of each SNP, insertion, and deletion is indicated proximal to the markings described. Exons are bounded by boxes to differentiate exon and intron sequences. Exon and intron numbers are also indicated in the margins. The start codon is indicated by a box within exon 2, and the stop codon, as well as two polyadenylation signal sequences, are indicated by boxes within exon 8. FIG. 1A (SEQ ID NO:1, top strand; SEQ ID NO:32, bottom strand) includes 5' flanking region, exon 1, and part of intron 1; FIG. 1B (SEQ ID NO:27, top strand; SEQ ID NO:33, bottom strand) includes part of intron 1, exon 2, intron 2, exon 3, and part of intron 3; FIG. 1C (SEQ ID NO:28, top strand; SEQ ID NO:34, bottom strand) includes part of intron 3, exon 3b, and part of intron 3; FIG. 1D (SEQ ID NO:29, top strand; SEQ ID NO:35, bottom strand) includes part of intron 3, exon 4, and part of intron 4. Positions 1–355 correspond to nucleotides −354 to −1 of intron 3. Positions 356–453 correspond to nucleotides 278 to 375 of the cDNA sequence. Positions 454–799 correspond to nucleotides 1 to 346 of intron 4; FIG. 1E (SEQ ID NO:30, top strand; SEQ ID NO:36, bottom strand) includes part of intron 4, exon 5, intron 5, exon 6, intron 6, exon 7, and part of intron 7; FIG. 1F (SEQ ID NO:31, top strand; SEQ ID NO:37, bottom strand) includes part of intron 7, exon 8, and a 3' flanking region. Positions 1–360 correspond to nucleotides −360 to −1 of intron 7. Positions 361–721 correspond to nucleotides 779 to 1139 of the cDNA sequence. Intron 3 is approximately 7.0 kilobases, intron 4 is approximately 3.8 kilobases, and intron 7 is approximately 3.0 kilobases.

FIG. 2A (SEQ ID NO:26) and 2B (SEQ ID NO:2) are the cDNA and amino acid sequences of the reference SULT1C1, respectively.

DETAILED DESCRIPTION

Figure 3:
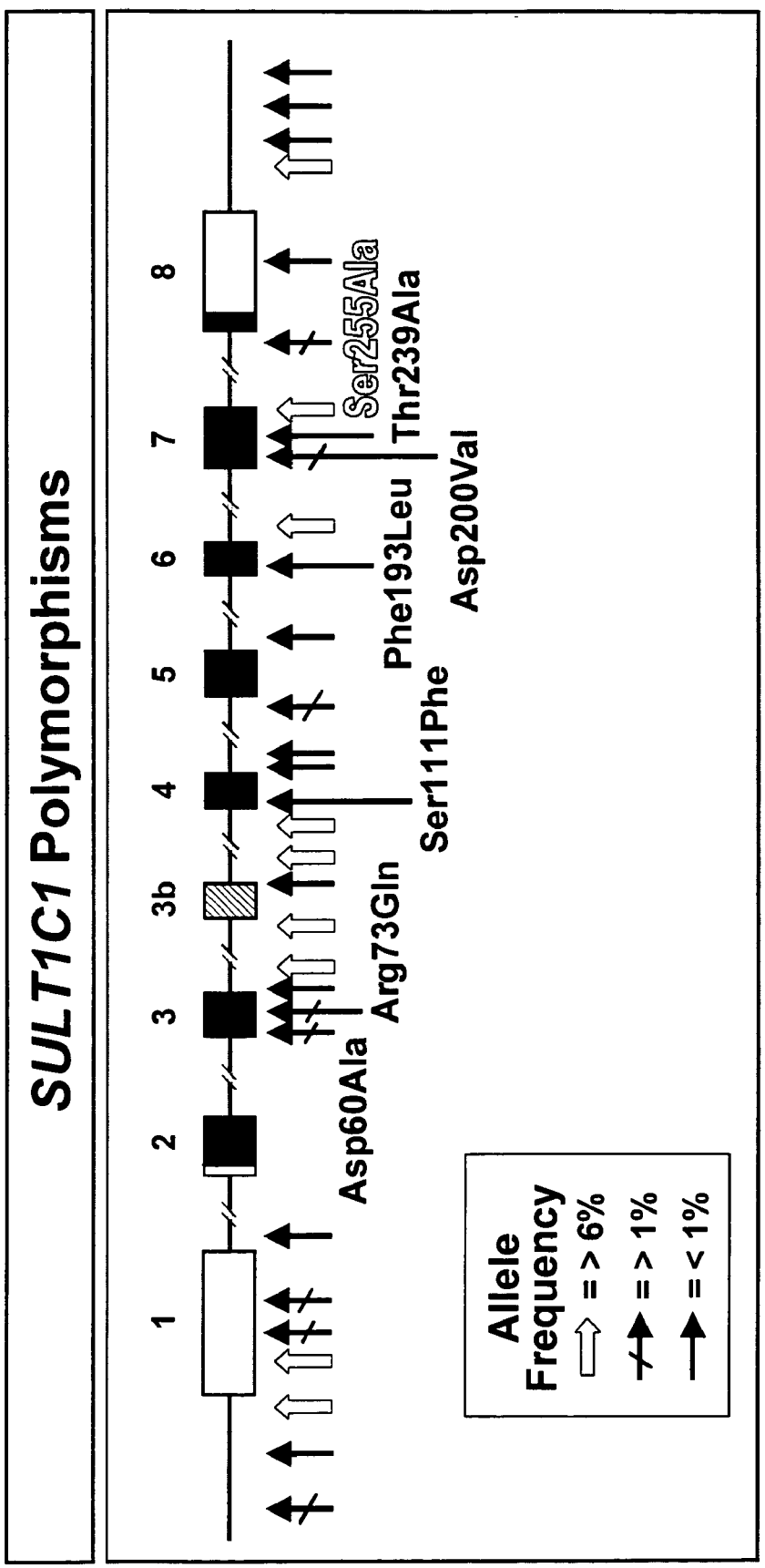
FIG. 3 is a schematic of the location of the non-synonymous polymorphisms within the SULT1C1 sequence.

The invention features SULT1C1 nucleotide and amino acid sequence variants. SULT1C1 catalyzes the transfer of inorganic sulfate to planar phenols, including hydroxyarylamines, and uses 3'-phosphoadenosine-5'-phosposulfate (PAPS) as the sulfate donor. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. For example, SULT1C1 may play a role in thyroid hormone inactivation. Thyroid hormone levels are determined primarily by sulfation, which increases the rate of deiodination and subsequent inactivation. Sulfation of certain compounds, however, such as the hydroxy metabolite of 2-acetylaminofluorene (AAF), produces sulfate conjugates that are chemically unstable and that can degrade to form reactive, electrophilic species. In particular, sulfation of the hydroxy metabolite of AAF produces a reactive N—O-sulfate ester, which can rearrange and fragment into a reactive electrophilic species that can bind to nucleic acids and proteins. Thus, detecting sulfotransferase nucleic acid and amino acid sequence variants facilitates the prediction of therapeutic efficacy and toxicity of drugs on an individual basis, as well as the ability to biotransform certain hormones and neurotransmitters.

Nucleic Acid Molecules

The invention features isolated nucleic acids that include a SULT1C1 nucleic acid sequence. The SULT1C1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT1C1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10–20 (e.g., 11, 12, 13, 14, 15, 16, 17, 18, 19, or 20 nucleotides in length), 20–50, 50–100 or greater than 100 nucleotides in length (e.g., greater than 150, 200, 250, 300, 350, 400, 450, 500, 750, or 1000 nucleotides in length). Nucleic acids of the invention can be in sense or antisense orientation, can be complementary to the SULT1C1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187–195; and Hyrup et al. (1996) *Bioorgan. Med. Chem.* 4(1):5–23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT1C1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference SULT1C1 nucleic acid sequence is provided in FIG. 1 (SEQ ID NOS:1, 27, 28, 29, 30, and 31) and in GenBank (Accession Nos. U66036, AF186251–AF186256, and AF186257–AF186262). The reference SULT1C1 amino acid sequence is provided in FIG. 2B (SEQ ID NO:2) and in GenBank (Accession No. U66036). The nucleic acid and amino acid reference sequences also are referred to herein as "wild type". As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences are designated as "−X" relative to the "A" in the initiation codon; positions of nucleotide sequence variants in the coding sequence and 3' untranslated sequence are designated as "+X" or "X" relative to the "A" in the initiation codon. Nucleotide sequence variants that occur in introns are designated as "+X" or "X" relative to "G" in the splice donor site (GT) or as "−X" relative to the "G" in the splice acceptor site (AG).

In some embodiments, a SULT1C1 nucleotide sequence variant encodes a SULT1C1 polypeptide having an altered amino acid sequence. The term "polypeptide" refers to a chain of at least four amino acid residues (e.g., 4–8, 9–12, 13–15, 16–18, 19–21, 22–100, 100–150, 150–200, 200–300 residues, or a full-length SULT1C1 polypeptide). SULT1C1 polypeptides may or may not have sulfotransferase catalytic activity, or may have altered activity relative to the reference SULT1C1 polypeptide. Polypeptides that do not have activity or have altered activity are useful for diagnostic purposes (e.g., for producing antibodies having specific binding affinity for variant sulfotransferase polypeptides).

Corresponding SULT1C1 polypeptides, irrespective of length, that differ in amino acid sequence are herein referred to as allozymes. For example, a SULT1C1 nucleic acid sequence that includes a cytosine at nucleotide 179 encodes a SULT1C1 polypeptide having an alanine at amino acid residue 60. This polypeptide (Asp60Ala) would be considered an allozyme with respect to the reference SULT1C1 polypeptide that contains an aspartic acid at amino acid residue 60. Additional non-limiting examples of SULT1C1 sequence variants that alter amino acid sequence include variants at nucleotides 218, 332, 577, 599, 715, and 763. For example, a SULT1C1 nucleic acid molecule can include an adenine at nucleotide 218 and encode a SULT1C1 polypeptide having a glutamine at amino acid residue 73 in place of an arginine residue (Arg73Gln); a thymine at nucleotide 332 and encode a SULT1C1 polypeptide having a phenylalanine at amino acid 111 in place of a serine (Ser111Phe); a cytosine at nucleotide 577 and encode a SULT1C1 polypeptide having a leucine residue at amino acid 193 in place of a phenylalanine (Phe193Leu); a thymine at nucleotide 599 and encode a SULT1C1 polypeptide having a valine at amino acid 200 in place of an aspartic acid (Asp200Val); a guanine at nucleotide 715 and encode a SULT1C1 polypeptide having an alanine at amino acid 239 in place of a threonine (Thr239Ala); or a guanine at nucleotide 763 and encode a SULT1C1 polypeptide having an alanine at amino acid 255 in place of a serine (Ser255Ala). In addition, a SULT1C1 nucleic acid can encode an allozyme having two or more amino acid variants, e.g., the nucleic acid can have variations at nucleotides 599 and 715, 179 and 763, and 218 and 763.

SULT1C1 allozymes as described above are encoded by a series of sulfotransferase alleles. These alleles represent nucleic acid sequences containing sequence variants, typically multiple sequence variants, within coding and non-coding sequences. Representative examples of single nucleotide variants are described above. Table 4 sets out a series of SULT1C1 alleles that encode SULT1C1. Alleles encoding Arg73Gln, Asp200Val, and Ser255Ala are commonly observed (allele frequencies >1%). The relatively large number of alleles and allozymes for SULT1C1 indicates the potential complexity of SULT pharmacogenetics. Such complexity emphasizes the need for determining single nucleotide variants, (i.e., single nucleotide polymorphisms, SNPs) as well as complete haplotypes (i.e., the set of alleles on one chromosome or a part of a chromosome) of patients.

Certain SULT1C1 nucleotide sequence variants do not alter the amino acid sequence. Such variants, however, could alter regulation of transcription as well as mRNA stability. SULT1C1 variants can occur in intron sequences, for example, within introns 1, 2, 3, 4, 5, 6, or 7. In particular, the nucleotide sequence variant can include a cytosine at nucleotide 37 of intron 1. Intron 3 variants can include a deletion of "CT" at 61–62, a deletion of a 30 bp sequence at 107 (5'-TCTCTCCTTCCTCTTTTCTCTCTCCCTCCC-3', SEQ ID NO:3), insertion of a thymine at −2377, substitution of a thymine at −2177, substitution of a thymine at −2158, or substitution of an adenine at −80. Intron 4 variants include substitution of an adenine at 68, a cytosine at 94, or a thymine at −20. Intron 5 sequence variants can include substitution of an adenine at 97. Intron 6 sequence variants can include a substitution of a guanine at 73. Intron 7 variants can include an insertion of an adenine at −101.

SULT1C1 nucleotide sequence variants that do not change the amino acid sequence also can be within an exon or in 5' or 3' untranslated sequences. For example, the 5' flanking region of SULT1C1 can include a substitution of a guanine at −760, a guanine at −547, a thymine at −518, or a cytosine at −500 and the 5' UTR can include a substitution of a thymine at −258 or an insertion of a cytosine at −149. The 3' UTR can contain a cytosine at 1027 and the 3' flanking region can include a guanine at 1191, a guanine at 1217, a guanine at 1251, and a cytosine at 1260.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT1C1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis *Genetic Engineering News*, 12(9):1 (1992); Guatelli et al., *Proc. Natl. Acad. Sci. USA*, 87:1874–1878 (1990); and Weiss, *Science*, 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, Edited by Ausubel, F. M et al., 1992. Examples of positions that can be modified are described above.

SULT1C1 Polypeptides

Isolated SULT1C1 polypeptides of the invention include an amino acid sequence variant relative to the reference SULT1C1 (FIG. 2, GenBank Accession No. U66036). The term "isolated" with respect to a SULT1C1 polypeptide refers to a polypeptide that has been separated from cellular components that naturally accompany it. Typically, the polypeptide is isolated when it is at least 60% (e.g., 70%, 80%, 90%, 95%, or 99%), by weight, free from proteins and naturally-occurring organic molecules that are naturally associated with it. In general, an isolated polypeptide will yield a single major band on a non-reducing polyacrylamide gel.

SULT1C1 polypeptides of the invention include variants at one or more of residues 60, 73, 111, 193, 200, 239, and 255. In particular, an alanine residue can be substituted at position 60, a glutamine residue at position 73, a phenylalanine at position 111, a leucine at position 193, a valine at position 200, an alanine at position 239, or an alanine at position 255. SULT1C1 polypeptides may have more than one amino acid substitution. For example, a SULT1C1 polypeptide can have a valine at amino acid 200 and an alanine at amino acid 239, an alanine at amino acid 60 and an alanine at amino acid 255, or a glutamine at amino acid 73 and an alanine at amino acid 255.

In some embodiments, activity of SULT1C1 polypeptides is altered relative to the reference SULT1C1. As described herein, certain SULT1C1 allozymes have reduced activity (e.g., Asp60Ala, Arg73Gln, Ser111Phe, Phe193Leu, Asp200Val, Thr239Ala, and Asp200Val, Thr239Ala), while other allozymes (Ser255Ala) have activity that is comparable to the reference SULT1C1. Other allozymes can have increased activity relative to the reference SULT1C1. Activity of SULT1C1 polypeptides can be assessed in vitro using a sulfate acceptor substrate such as 4-nitrophenol (4-NP, Sigma Chemical Co., St. Louis, Mo.) and a donor sulfate molecule such as PAPS. In general, recombinant SULT1C1 polypeptides can be incubated at 37° C. with 10 mM of sulfate acceptor substrate in a potassium phosphate buffer (5 mM, pH 7.4) and 0.4 µM labeled PAPS (e.g., $^{35}$S-PAPS from New England Nuclear Life Science Products, Inc., Boston Mass.). Reactions can be stopped by precipitating PAPS and SULT1C1 polypeptide (e.g., with barium hydroxide, barium acetate, and zinc sulfate). After centrifugation of the reaction, radioactivity in the supernatant is assessed. SULT1C1 activity is expressed as nmoles of sulfate conjugated product formed per hour of incubation. See, Campbell, N. R. C. et al., *Biochem. Pharmacol.*, 36:1435–1446 (1987).

Other biochemical properties of allozymes, such as apparent Km values, also can be altered relative to the reference SULT1C1. Apparent Km values can be calculated, for example, by using the method of Wilkinson with a computer program written by Cleland. Wilkinson, *Biochem. J.*, 80:324–332 (1961); and Cleland, *Nature*, 198:463–365 (1963). As described herein, the apparent Km values for PAPS vary 7-fold among the allozymes tested (Asp60Ala, Arg73Gln, Phe193Leu, Asp200Val, Thr239Ala, and Ser255Ala).

Isolated polypeptides of the invention can be obtained, for example, by extraction from a natural source (e.g., liver tissue), chemical synthesis, or by recombinant production in a host cell. To recombinantly produce SULT1C1 polypeptides, a nucleic acid sequence encoding a sulfotransferase variant polypeptide can be ligated into an expression vector and used to transform a bacterial or eukaryotic host cell (e.g., insect, yeast, or mammalian cells). In general, nucleic acid constructs include a regulatory sequence operably linked to a sulfotransferase nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express sulfotransferase variant polypeptides. A nucleic acid encoding a polypeptide of the invention can be cloned into, for example, a baculoviral vector such as pBlueBac (Invitrogen, San Diego, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Mammalian cell lines that stably express sulfotransferase variant polypeptides can be produced by using expression vectors with the appropriate control elements and a selectable marker. For example, the eukaryotic expression vector pCR3.1 (Invitrogen, San Diego, Calif.) and p91023(B) are suitable for expression of sulfotransferase variant polypeptides in, for example, Chinese hamster ovary (CHO) cells, COS-1 cells, human embryonic kidney 293 cells, NiH3T3 cells, BHK21 cells, MDCK cells, and human vascular endothelial cells (HUVEC). Following introduction of the expression vector by electroporation, liptofectin, calcium phosphate or calcium chloride co-precipitation, DEAE dextran, or other suitable method, stable cell lines are selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

SULT1C1 variant polypeptides can be purified by known chromatographic methods including DEAE ion exchange, gel filtration, and hydroxylapatite chromatography. Van Loon and Weinshilboum, *Drug Metab. Dispos.*, 18:632–638 (1990); Van Loon et al., *Biochem. Pharmacol.*, 44:775–785 (1992). SULT1C1 polypeptides can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase. Immunoaffinity chromatography also can be used to purify SULT1C1 polypeptides.

Non-Human Mammals

The invention features non-human mammals that include SULT1C1 nucleic acids of the invention, as well as progeny and cells of such non-human mammals. Non-human mammals include, for example, rodents such as rats, guinea pigs, and mice, and farm animals such as pigs, sheep, goats, horses and cattle. Non-human mammals of the invention can express a SULT1C1 variant nucleic acid in addition to an endogenous SULT1C1 (e.g., a transgenic non-human that includes a SULT1C1 nucleic acid randomly integrated into the genome of the non-human mammal). Alternatively, an endogenous SULT1C1 nucleic acid can be replaced by a SULT1C1 variant nucleic acid of the invention through homologous recombination. See, Shastry, B. S., *Mol. Cell Biochem.*, (1998) 181(1–2):163–179, for a review of gene targeting technology.

In one embodiment, non-human mammals are produced that lack an endogenous SULT1C1 nucleic acid (i.e., a knockout), then a SULT1C1 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B- phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent". Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT1C1 nucleic acid. That is, cultured ES cells can be transformed with a knockout construct and cells selected in which the SULT1C1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37–9.52 of Sambrook et al., "Molecular Cloning, A Laboratory Manual, second edition, Cold Spring Harbor Press, Plainview; NY, 1989.

To generate a knockout animal, ES cells having at least one inactivated SULT1C1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated SULT1C1 allele. If the original ES cell was heterozygous for the inactivated SULT1C1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are "totipotent", i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT1C1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated SULT1C1 gene, and then fused with enucleated oocytes. After activation of the oocytes, the eggs are cultured to the blastocyst stage, and implanted into a recipient. See, Cibelli, J. B. et al., *Science*, (1998) 280: 1256–1258. Adult somatic cells, including, for example, cumulus cells and mammary cells, can be used to produce animals such as mice and sheep, respectively. See, for example, Wakayama, T. et al., *Nature*, (1998) 394(6691): 369–374; and Wilmut, I. et al., *Nature*, (1997) 385(6619): 810–813. Nuclei can be removed from genetically modified adult somatic cells, and transplanted into enucleated oocytes. After activation, the eggs can be cultured to the 2–8 cell stage, or to the blastocyst stage, and implanted into a suitable recipient. Wakayama, T. et al., 1998, supra.

Non-human mammals of the invention such as mice can be used to screen, for example, toxicity of compounds that are substrates for SULT1C1, drugs that alter SULT1C1 activity, or for carcinogenesis. For example, SULT1C1 activity or toxicity can be assessed in a first group of such non-human mammals in the presence of a compound, and compared with SULT1C1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting Sulfotransferase Sequence Variants

Sulfotransferase nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33–39), denaturing high performance liquid chromatography (DHPLC, Underhill et al., 1997, *Genome Res.*, 7:996–1005), infared matrix-assisted laser desorption/ionization (IR- MALDI) mass spectrometry (WO 99/57318), and combinations of such methods.

Genomic DNA generally is used in the analysis of sulfotransferase nucleotide sequence variants. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizards Genomic DNA purification kit (Promega, Madison, Wis.) and the A.S.A.P.™ Genomic DNA isolation kit (Boehringer Mannheim, Indianapolis, Ind.).

Typically, an amplification step is performed before proceeding with the detection method. For example, exons or introns of the sulfotransferase gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al., 1991, *Am. J. Hum. Genet.* 48:370–382; and Prince et al., 2001, *Genome Res.*, 11(1): 152–162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2× SSC (0.3M NaCl/0.03 M sodium citrate/0.1% sodium dodecyl sulfate (SDS) and washed in 0.1× SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For SULT1C1 sequence variants that do not alter a common restriction site, mutagenic primers can be designed that introduce a restriction site when the variant allele is present or when the wild type allele is present. A portion of SULT1C1 nucleic acid can be amplified using the mutagenic primer and a wild type primer, followed by digest with the appropriate restriction endonuclease.

Certain variants, such as insertions or deletions of one or more nucleotides (e.g., deletion of a 30 bp sequence in intron 3), change the size of the DNA fragment encompassing the variant. The insertion or deletion of nucleotides can be assessed by amplifying the region encompassing the variant and determining the size of the amplified products in comparison with size standards. For example, the intron 3 region of SULT1C1 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163–169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, sulfotransferase variants can be detected by antibodies that have specific binding affinity for variant sulfotransferase polypeptides. Variant sulfotransferase polypeptides can be produced in various ways, including recombinantly, as discussed above. Host animals such as rabbits, chickens, mice, guinea pigs and rats can be immunized by injection of a sulfotransferase variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a sulfotransferase variant polypeptide and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77–96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a sulfotransferase variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of sulfotransferase variant polypeptides by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992.

Methods of the Invention

As a result of the present invention, it is now possible to determine sulfonator status of a mammal (e.g., a human subject) as well as to determine if a mammal is predisposed to thyroid disease or cancer. "Sulfonator status" refers to the ability of a mammal to transfer a sulfate group to a substrate (e.g., thyroid hormone). Predisposition refers to a relative greater risk for development of a disease such as hypothyroidism or hyperthyroidism, or a chemically induced cancer. Presence of SULT1C1 allozymes with reduced activity may indicate a relatively reduced risk for development of a chemically induced cancer. Additional risk factors including, for example, family history and other genetic factors can be considered when determining risk. Predisposition to thyroid disease or cancer can be determined based on the presence or absence of a single sulfotransferase sequence variant or based on a variant profile. "Variant profile" refers to the presence or absence of a plurality (i.e., two or more sequence variants) of SULT1C1 nucleotide sequence variants or SULT1C1 amino acid sequence variants. For example, a variant profile can include the complete SULT1C1 haplotype of the mammal or can include the presence or absence of a set of common non-synonymous SNPs (i.e., single nucleotide substitutions that alter the amino acid sequence of a SULT1C1 polypeptide). In one embodiment, the variant profile includes detecting the presence or absence of three or more non-synonymous SNPs (e.g., 3, 4, 5, 6, or 7 non-synonymous SNPs and combinations thereof) described above.

Articles of Manufacture

Articles of manufacture of the invention include populations of isolated SULT1C1 J nucleic acid molecules or SULT1C1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT1C1 nucleic acid or SULT1C1 polypeptide sequence variant. Such articles of manufacture can include two or more sequence variants of SULT1C1, or can include all of the sequence variants known for SULT1C1. Furthermore, nucleic acid molecules containing sequence variants for other sulfotransferases, such as SULT1C1, SULT1A2, SULT1A3, and SULT1A2, can be included on the substrate. See, WO 99/64630 and WO 00/20605 for a description of other SULT1C1, SULT1A2, SULT1A3, and SULT1A2 sequence variants.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.*, 14:441–447 (1996); and U.S. Pat. Nos. 5,770,722 and 5,733,729.

The invention will be further described in the following examples, which do not limit the scope of the invention described in the claims.

EXAMPLES

Example 1

Methods and Materials: PCR Amplification and DNA Sequencing Blood samples were obtained from 89 randomly selected Caucasian blood donors (61 women, 28 men) at the Mayo Clinic Blood Bank in Rochester, Minn. Genomic DNA was extracted from each blood sample using QIAamp Blood Kits (Qiagen, Valencia, Calif.). Once extracted, the genomic DNA was used as template for PCR with SULT1C1-specific primers. To make it possible to sequence SULT1C1, the 9 exons in the gene, including the initial untranslated exon and an alternatively-spliced exon located within intron 3 (exon 3b), were amplified from each of the 89 DNA samples by use of PCR. Specifically, PCR primers were designed that flanked the exons and that would produce amplification products 400–500 bp in length. Two overlapping amplifications were required for the first and last exons because of their lengths. Therefore, 11 separate amplifications were performed for each DNA sample. Dye primer DNA sequencing chemistry was used to facilitate the identification of heterozygous bases. To make that possible, M13 sequence tags were added to the 5' ends of each primer. Locations of primers were chosen to avoid repetitive sequence and to ensure amplification specificity. The sequences and locations of each primer within the gene are listed in Table 1. All forward primers contained the M13 forward sequence, and all reverse primers contained the M13 reverse sequence to make it possible to use dye primer DNA sequencing chemistry. "F" represents forward; "R", reverse; "U", upstream; "D", downstream; "I", intron; "FR", flanking region; and "UTR", untranslated region.

was also analyzed visually, independent of the PolyPhred analysis, and polymorphism "calls" from these two independent analyses were compared. The University of Wisconsin GCG software package, Version 10, was also used to analyze nucleotide sequence.

COS-1 Cell Expression: Nine different SULT1C1 expression constructs were made using the p91023(B) expression vector. See, Wong et al., *Science* (1985) 228:810–815, for a description of the p91023(B) vector. Eight of the constructs were designed to express variant SULT1C1 polypeptides, while the remaining construct was designed to express a wild type SULT1C1. All SULT1C1 cDNA sequences used to create the expression constructs were created by site directed mutagenesis using the method described by Ho et al., *Gene* (1989) 77(1):51–9. Each SULT1C1 cDNA was amplified by PCR and subcloned into the EcoRI restriction site of the eukaryotic expression vector p91023(B). After subcloning, all inserts were sequenced to assure that no spurious nucleotide point mutations had been introduced during the PCR amplifications. COS-1 cells were transfected with these

TABLE 1

PCR primers used for SULT1C1 resequencing

| Primer Name | Primer Location | 5'-M13 tag | - | Primer Sequence Gene Specific Primer-3' | SEQ ID NO: |
|---|---|---|---|---|---|
| UF (−807) M13 | 5'-FR | TGTAAAACGACGGCCAGT | - | GTACAATAAGGCAAAGAAAAAATAAGTACACACCTAAG | 4 |
| UR (−357) M13 | 5'-UTR | CAGGAAACAGCTATGACC | - | CACTCTACTCCTCCTCTCGGTCAC | 5 |
| UF (−405) M13 | 5'-UTR | TGTAAAACGACGGCCAGT | - | GGAAAGATGTGAAAAACTCTAGTCGGTGAC | 6 |
| I1R99 M13 | | CAGGAAACAGCTATGACC | - | TTTGAATAAATGCATCTGTAAAGCCACACCTATGT | 7 |
| I1F(−120) M13 | Intron 1 | TGTAAAACGACGGCCAGT | - | AATGTGAATGTACTTAATGCCTCTGAACTGTACAC | 8 |
| I2R112 M13 | Intron 1 | CAGGAAACAGCTATGACC | - | CATTGTGGAACAATAAGAAGGAGCAGGTTTC | 9 |
| I2F275 M13 | Intron 2 | TGTAAAACGACGGCCAGT | - | ATGGCAAACAGGATTCTGACCCAAGGG | 10 |
| I3R186 M13 | Intron 2 | CAGGAAACAGCTATGACC | - | GAAACATATGACAGTGAAAATGAGAGAGAAAGAGA | 11 |
| I3F(−2464) M13 | Intron 3 | TGTAAAACGACGGCCAGT | - | GCACTTTTTTTTGAGACAGGGTCTCACTCTG | 12 |
| I3R(−2040) M13 | Intron 3 | CAGGAAACAGCTATGACC | - | GGGAAAAGCCCTATGAACAAGAGCTAGAAAA | 13 |
| I3F(−151) M13 | Intron 3 | TGTAAAACGACGGCCAGT | - | ATTAATAATCCCATTGTAAAATCCCAAAAGAAAGTCAAG | 14 |
| I4R155 M13 | Intron 3 | CAGGAAACAGCTATGACC | - | GCTGAATGTAGAACTTTATGTTTTCTCTTTGCTGGTA | 15 |
| I4F(−114) M13 | Intron 4 | TGTAAAACGACGGCCAGT | - | AGGGCCAGCACTGCAGAACTGAG | 16 |
| I5R155 M13 | Intron 4 | CAGGAAACAGCTATGACC | - | ACACTCAGTGGCCAGCTTGCTCTG | 17 |
| I5F313 M13 | Intron 5 | TGTAAAACGACGGCCAGT | - | CTACACCACCCTCAAAATCAAACAGATCAG | 18 |
| I6R146 M13 | Intron 5 | CAGGAAACAGCTATGACC | - | GCGGCAAGGGTAACATTGGACTGGAAT | 19 |
| I6F91 M13 | Intron 6 | TGTAAAACGACGGCCAGT | - | TGTAGTATTTCTTTATGATACTCTCATTCATTCCAGTC | 20 |
| I7R171 M13 | Intron 6 | CAGGAAACAGCTATGACC | - | CTAGAAAGCTCTCTTCTACAACAGGATCAAATC | 21 |
| I7F(−184) M13 | Intron 7 | TGTAAAACGACGGCCAGT | - | ACCGAGTCCCCTAGGCCTGCTTCTTATA | 22 |
| SULT1C1R1008 M13 | Intron 7 | CAGGAAACAGCTATGACC | - | GTACTACATTGTATACATTCACAATATGCTTTCAGAG | 23 |
| | 3'-UTR | TGTAAAACGACGGCCAGT | - | ACTATCTTCAATCCTTCAGTCCCAGCCA | 24 |
| SULT1C1F937 M13 | 3'-UTR | CAGGAAACAGCTATGACC | - | GAGTTCGGTGAATGGCCAGGACAG | 25 |
| DR1305 M13 | 3'-FR | | | | |

DNA sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

DNA sequence analysis: The PolyPhred 3.0 and Consed 8.0 programs were used to analyze the DNA sequence chromatograms for polymorphic sites. Each chromatogram expression constructs by the TransFast™ reagent (Promega, Madison, Wis.) as suggested by the manufacturer (i.e., using a 1:1 charge ratio). As a control, a transfection was also performed with "empty" p91023(B), i.e., vector lacking an insert, to make it possible to correct for endogenous COS-1 cell SULT activity. The control plasmid pSV-β-galactosidase (Promega, Madison, Wis.) was cotransfected with each SULT1C1 construct to make it possible to correct for transfection efficiency. Two independent transfections, each consisting of three separate plates, were performed with each of the expression constructs. After 48 hours in culture, the transfected cells were harvested and high speed supernatant (HSS) cytosol preparations were prepared as described by Wood, T. C. et al., *Biochem. Biophys. Res. Commun.*, 198:1119–1127 (1994). Aliquots of these cytosol preparations were stored at −80° C. prior to assay.

Enzyme Assays: β-galactosidase activity in each of the COS-1 HSS preparations was measured with the β-galactosidase Enzyme Assay System (Promega, Madison, Wis.). SULT1C1 enzyme activity was measured with an assay that involves sulfate conjugation of a sulfate acceptor substrate, 4-nitrophenol (4-NP), in the presence of [$^{35}$S]-3'-phosphoadenosine-5'-phosphosulfate (PAPS), the sulfate donor for the reaction. See, Campbell, N. R. C. et al., *Biochem. Pharmacol.*, 36:1435–1446 (1987). The HSS preparations of recombinant SULT1C1 variant proteins described above were used for the activity studies without any further purification. The protein concentration of each recombinant protein preparation was determined by the dye-binding method of Bradford with bovine serum albumin (BSA) as a standard. Briefly, 0.4 μM 35-PAPS was used as the sulfate donor with 10 mM 4-NP as the sulfate acceptor substrate in 5 mM potassium phosphate buffer at pH 7.4. Blanks were samples that did not contain 4-NP. Cytosol from COS-1 cells that had been transfected with empty p91023(B) was used to correct for endogenous SULT activity. Because SULTs display profound substrate inhibition, 4-NP concentrations that ranged from 100 μM to 10 mM were tested with each recombinant allozyme to ensure that the assays were performed at 4-NP concentrations that yielded maximal activity for that allozyme. Enzyme activity was expressed as nanomoles (nmoles) of sulfate conjugated product formed per hour of incubation. Apparent $K_m$ values for PAPS were determined in the presence of 10 mM 4-NP with six PAPS concentrations that varied from 0.0625 μM to 2 μM. As described subsequently, it was not possible to determine apparent $K_m$ values for 4-NP.

Data Analysis: Apparent $K_m$ values were calculated by using the method of Wilkinson with a computer program written by Cleland. Wilkinson, G. N., *Biochem. J.*, 80:324–332 (1961); and Cleland, W. W., *Nature*, 198:463–365 (1963). Statistical comparisons of data were performed by ANOVA with the StatView program, version 4.5 (Abacus Concepts, Inc., Berkeley, Calif.).

Western blot analysis: Quantitative Western blot analysis was performed with recombinant SULT1C1 protein. The quantity of cytosol loaded on the gel for each allozyme was adjusted so that each lane contained an equal quantity of β-galactosidase activity, i.e. gel loading was corrected for variation in transfection efficiency. Properties of the antibody used to detect the SULT1C1 protein have been described elsewhere. Bound antibody was detected by use of the ECL system (Amersham Pharmacia, Piscataway, N.J.). The Ambis densitometric system was used to quantitate immunoreactive protein in each lane, and those data were expressed as a percent of the intensity of the control wild type SULT1C1 protein band on that gel.

Example 2

SULT1C1 Polymorphisms: Eleven separate SULT1C1 PCR amplifications were performed for each of the 89 individual human genomic DNA samples studied. These reactions generated a total of approximately 900,000 bp of sequence. This sequence was analyzed both visually and by use of the PolyPhred software. These two analyses were performed by separate, independent observers. There were only three discrepancies in the polymorphism calls between the two methods. Two of these differences were the result of homozygous, single nucleotide sequence alterations present in single samples (at positions −760 and 599), which PolyPhred identified as differences from the consensus sequence. The third discrepancy involved a single heterozygous SNP at cDNA ORF nucleotide position 577 that was not called by PolyPhred. Therefore, the software had an advantage over a trained observer for the detection of homozygous variant sequences that might not be noticed as a result of variance in peak height, but it occasionally failed to call heterozygous variants. In addition, the software was not ideal for the evaluation of large insertion/deletion events such as the 30 bp insertion/deletion that was observed in SULT1C1 intron 3. Of the sequence analyzed, 92.9% was sequenced on both strands, making it possible to use data from the opposite strand to verify polymorphism calls. The most common reason for failure to sequence both strands was the presence of insertion/deletion events. All sequences were compared to the SULT1C1 gene sequences of GenBank accession numbers AF186257 to AF186262.

Sequencing of the 5' and 3' untranslated sequences, exons, and introns of the SULT1C1 nucleic acid revealed 31 variations, including 26 single nucleotide polymorphisms (SNPs), three insertions, and two deletions in SULT1C1 nucleic acid sequences (Table 1). Polymorphisms in exons, untranslated regions (UTR), and flanking regions (FR) are numbered relative to the adenine in the SULT1C1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). Asterisks indicate insertions or deletions. For the 5 insertions/deletions, alleles that lack the inserted sequence are denoted by a dash. 13(107) is a 30 bp deletion, denoted by "Ins" in the wild type sequence column. The insertions at −149, 13(−2377), and 17(−101) each involve a single nucleotide. The inserted nucleotide constitutes the variant in all three cases. The deletion at 13(61–62) involves a dinucleotide (CT) that is present in the wild type sequence and absent in the variant sequence. The deletion at 13(107) involves a 30 nucleotide fragment (5'-TCTCTCCTTCCTCTTTTCTCTCTC-CCTCCC-3'; SEQ ID NO: 3) that is present in the wild type sequence and absent in the variant sequence. Seven of the 26 SNPs altered the encoded amino acid (i.e., a non-synonymous SNP), resulting in seven different single variant SULT1C1 allozymes and one double variant SULT1C1 allozyme.

The SULT1C1 cDNA sequence was used to search the EST database, and the 39 EST sequences identified were screened for the presence of the polymorphisms observed during the resequencing experiments. Only the initial 400 bp of each EST sequence was used for this comparison to assume sequence quality. None of the 7 nonsynonymous cSNPs were observed in these EST sequences. Polymorphisms that were observed only once (one allele out of the 178 sequenced) accounted for 14 of the 31 observed polymorphism. An additional 6 polymorphisms were observed twice (2 as homozygous and 4 as heterozygous samples). The average number of polymorphisms present both in the gene overall and within the ORF was 7.9 per kb sequenced (Table 2). For purposes of comparison, Table 2 also includes data from a large study of polymorphism frequencies in 74 human genes (Halushka et al., *Nat. Genet.* (1999) 22(3):

239–247). Because Halushka et al. studied a slightly smaller number of samples (74 versus the 89 described), low frequency polymorphisms that would not have been detected by Halushka et al. have been eliminated because of their lower sample number. The genetic variation present within the SULT1C1 sequence was very similar to average values observed in the 74 genes sequenced by Halushka et al. The data in Table 2 are also presented by gene region, with "UTR" representing exons encoding cDNA untranslated regions and "FR" representing both 5'- and 3'-flanking regions.

TABLE 1

Human SULT1C1 polymorphisms and frequencies

| Polymorphism Position | Location In Gene | WT Sequence Nucleotide | Variant Sequence Nucleotide | Frequency |
|---|---|---|---|---|
| −760 | 5'-FR | T | G | 0.011 |
| −547 | 5'-FR | A | G | 0.006 |
| −518 | 5'-FR | C | T | 0.382 |
| −500 | 5'-FR | T | C | 0.208 |
| −258 | 5'-UTR | C | T | 0.011 |
| −149* | 5'-UTR | — | C | 0.022 |
| I1(37) | Intron 1 | T | C | 0.006 |
| 179 | Exon 3 | A | C | 0.011 |
| 218 | Exon 3 | G | A | 0.011 |
| I3(61–62)* | Intron 3 | CT | — | 0.006 |
| I3(107)* | Intron 3 | Ins/Ins | — | 0.416 |
| I3(−2377) | Intron 3 | — | T | 0.374 |
| I3(−2177) | Exon 3b | C | T | 0.006 |
| I3(−2158) | Intron 3 | C | T | 0.420 |
| I3(−80) | Intron 3 | G | A | 0.062 |
| 332 | Exon 4 | C | T | 0.006 |
| I4(68) | Intron 4 | C | A | 0.006 |
| I4(94) | Intron 4 | T | C | 0.006 |
| I4(−20) | Intron 4 | C | T | 0.045 |
| I5(97) | Intron 5 | T | A | 0.006 |
| 577 | Exon 6 | T | C | 0.006 |
| I6(73) | Intron 6 | A | G | 0.062 |
| 599 | Exon 7 | A | T | 0.011 |
| 715 | Exon 7 | A | G | 0.006 |
| 763 | Exon 7 | T | G | 0.067 |
| I7(−101)* | Intron 7 | — | A | 0.011 |
| 1027 | 3'-UTR | T | C | 0.006 |
| 1191 | 3'-FR | A | G | 0.073 |
| 1217 | 3'-FR | A | G | 0.006 |
| 1251 | 3'-FR | A | G | 0.006 |
| 1260 | 3'-FR | T | C | 0.006 |

TABLE 2

SULT1C1 polymorphism frequencies

Polymorphisms per kb

| | SULT1C1 | | |
|---|---|---|---|
| | Complete Data | Corrected | 74 Human Genes |
| Gene(s) | 1 | 1 | 74 |
| Samples | 89 | 89 | 75 |
| Min. Allele Freq. | 0.56% | 0.68% | 0.68% |
| Overall | 7.9 | 4.3 | 4.6 |
| Coding | 7.9 | 4.5 | 4.4 |
| Noncoding | 7.9 | 4.3 | 5.9 |
| UTR and FR | 9.5 | 5.2 | 4.4 |
| Introns | 6.9 | 3.7 | 6.0 |

The DNA samples used in these studies were obtained only from Caucasian subjects. Therefore, allele frequencies for these polymorphisms in a Caucasian population sample were calculated. Chi-square analysis indicated no significant gender-dependent differences in allele frequencies for any of the SULT1C1 polymorphisms found. The lowest allele frequency that was possible to detect was 0.56% since 89 DNA samples (178 alleles) were used. Those frequencies are also listed in Table 1. Overall, 17 of the 31 polymorphisms had allele frequencies greater than 1% and, as a result, may be considered "common" in the population sample. Five of the polymorphisms had allele frequencies greater than 10%. A total of eight SNPs were observed in the SULT1C1 coding region (FIG. 1 and Table 1), and only one of those cSNPs was synonymous (i.e, no change in amino acid sequence). This single synonymous cSNP was located in exon 3b, an exon that results from alternative splicing and is only rarely represented in mRNA. The other 7 cSNPs, all located in the exons that encode the wild type SULT1C1 protein, were nonsynonymous. Three of those nonsynonymous cSNPs were observed only once, 3 were seen twice and had allele frequencies of 1.1%, and one was present in 12 alleles, with a frequency of 6.7%. This common variant was T763G, designated SULT1C1*2, resulted in a Ser255Ala alteration in the encoded amino acid sequence. In addition to SNPs, 5 insertions/deletions were observed in SULT1C1 (FIG. 1 and Table 1). Three of those polymorphisms involved single bases, one was a two base change, and one consisted of a common 30 bp insertion/deletion in intron 3 that contained two 15 bp repeats. All of the allele frequencies for polymorphisms identified during the resequencing experiments, with two exceptions, conformed to the predictions of the Hardy-Weinberg theorum when the exact test was used (threshold $p<0.05$). Those two exceptions involved SNPs (−760 and 599), each of which was observed only as a homozygous change in a single sample. Studies of genetic polymorphisms are moving increasingly beyond merely dealing with single SNPs to also address the issue of haplotype, the combination of polymorphisms present within each allele. Therefore, linkage disequilibrium between individual polymorphisms was performed, along with common SULT1C1 haplotypes analysis.

Example 3

Linkage disequilibrium and haplotype analysis: Linkage disequilibrium analysis was performed after all of the DNA samples had been genotyped at each of the 31 polymorphic sites. The 10 polymorphisms with allele frequencies greater than 2.5% were chosen for inclusion in this analysis, since there was inadequate statistical power for the analysis of less common polymorphisms. All possible pairwise combinations of these 10 polymorphisms were tested for linkage disequilibrium using the EH program developed by Terwilliger and Ott, *Handbook of Human Genetic Linkage*, The Johns Hopkins University Press, Baltimore, pp. 188–193 (1994). The output of this program was used to calculate d' values, a method for reporting linkage data that is independent of sample size (Table 3). The genotype data were also used for haplotype analysis. In this case, unambiguous haplotype assignment could be made for samples that contained no more than one heterozygous locus. Haplotypes for some of the remaining alleles were inferred from the genotype data as well as the EM probabilities (Table 4).

TABLE 3

SULT1C1 linkage disequilibrium analysis

| Polymorphism Pair | | d' Value | $\chi^2$ Value |
|---|---|---|---|
| −518 | I3(107)* | −0.843 | 34.22 |
| I3(107)* | I3(−2377) | 0.852 | 34.05 |

TABLE 3-continued

SULT1C1 linkage disequilibrium analysis

| Polymorphism Pair | | d' Value | χ2 Value |
|---|---|---|---|
| I3(−2158) | I4(−20) | 1.000 | 8.84 |
| I3(−80) | I6(73) | 0.903 | 51.15 |
| I3(−80) | 763 | 0.902 | 48.45 |
| I3(−80) | 1191 | 0.900 | 45.24 |
| I6(73) | 763 | 1.000 | 61.80 |
| I6(73) | 1191 | 1.000 | 57.53 |
| 763 | 1191 | 0.909 | 52.07 |

TABLE 4

SULT1C1 haplotype analysis

| Name | Haplotype |
|---|---|
| A | I3(−2377) |
| B | −518, −500, I3(107) |
| C | −518, I3(107), I3(−2158) |
| D | I3(−2158) |
| B | I3(107), I3(−2158) |
| F | −518, I3(−2158) |
| G | I3(−2158), I4(−20) |
| H | I3(107), I3(−2158), I4(−20) |
| I | I3(107), I3(−2377) |
| J | −760, −500, I3(−2377) |
| K | −760, I3(−2377) |
| L | −518, I1(37), I3(107), I3(−2158) |
| M | I3(−2377), 1260 |
| N | 599, 715 |
| O | 179, 763 |
| P | 218, 763 |

Example 4

Activity of SULT1C1 allozymes: Cytosol preparations of recombinant SULT1C1 allozymes, were used to assess catalytic activities as described in Example 1. Resulting activities were adjusted to a percentage of the wild type SULT1C1 enzyme activity. The PAPS apparent $K_m$ values varied 7-fold, and seven of the eight enzymes exhibit reduced enzyme activity relative to the wild type SULT1C1 enzyme (Table 5).

TABLE 5

Recombinant human SULT1C1 biochemical properties

| Polymorphism | Amino Acid Change | % WT activity | Apparent $K_m$ |
|---|---|---|---|
| A179C | Asp60Ala | 13.9 ± 0.3 | 4.00 ± 0.47 |
| G218A | Arg73Gln | 14.5 ± 1.9 | 0.57 ± 0.15 |
| C332T | Ser111Phe | 0 | N.D. |
| T577C | Phe193Leu | 39.3 ± 1.4 | 2.95 ± 0.27 |
| A599T | Asp200Val | 48.1 ± 4.2 | 1.20 ± 0.12 |
| A715G | Thr239Ala | 52.6 ± 1.7 | 1.14 ± 0.11 |
| T763G | Ser255Ala | 98.9 ± 5.9 | 0.56 ± 0.06 |
| A599T/A715G | Asp200Val/Thr239Ala | 49.3 ± 2.8 | 1.82 ± 0.14 |
| wild type | none | 100 | 0.77 ± 0.04 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 1380 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CTTTAATTTT CTTTTATCTT ACTCTCCTAC ATAAGACATC AAGAAACAAT TGTATATTGT      60

ACACCCCCCC CCTCCACAAA CACAAATATT GATAATATAA AGATGTCTGC TGCTGCTGAT     120

AGATTAAACT TAACTTCCGG CCACTTGAAT GCTGGTAGAA AGAGAAGTTC CTCTTCTGTT     180

TCTTTGAAGG CTGCCGAAAA GCCTTTCAAG GTTACTGTGA TTGGATCTGG TAACTGGGGT     240
```

```
ACTACTATTG CCAAGGTGGT TGCCGAAAAT TGTAAGGGAT ACCCAGAAGT TTTCGCTCCA      300

ATAGTACAAA TGTGGGTGTT CGAAGAAGAG ATCAATGGTG AAAAATTGAC TGAAATCATA      360

AATACTAGAC ATCAAAACGT GAAATACTTG CCTGGCATCA CTCTACCCGA CAATTTGGTT      420

GCTAATCCAG ACTTGATTGA TTCAGTCAAG GATGTCGACA TCATCGTTTT CAACATTCCA      480

CATCAATTTT TGCCCCGTAT CTGTAGCCAA TTGAAAGGTC ATGTTGATTC ACACGTCAGA      540

GCTATCTCCT GTCTAAAGGG TTTTGAAGTT GGTGCTAAAG GTGTCCAATT GCTATCCTCT      600

TACATCACTG AGGAACTAGG TATTCAATGT GGTGCTCTAT CTGGTGCTAA CATTGCCACC      660

GAAGTCGCTC AAGAACACTG GTCTGAAACA ACAGTTGCTT ACCACATTCC AAAGGATTTC      720

AGAGGCGAGG GCAAGGACGT CGACCATAAG GTTCTAAAGG CCTTGTTCCA CAGACCTTAC      780

TTCCACGTTA GTGTCATCGA AGATGTTGCT GGTATCTCCA TCTGTGGTGC TTTGAAGAAC      840

GTTGTTGCCT TAGGTTGTGG TTTCGTCGAA GGTCTAGGCT GGGGTAACAA CGCTTCTGCT      900

GCCATCCAAA GAGTCGGTTT GGGTGAGATC ATCAGATTCG GTCAAATGTT TTTCCCAGAA      960

TCTAGAGAAG AAACATACTA CCAAGAGTCT GCTGGTGTTG CTGATTTGAT CACCACCTGC     1020

GCTGGTGGTA GAAACGTCAA GGTTGCTAGG CTAATGGCTA CTTCTGGTAA GGACGCCTGG     1080

GAATGTGAAA AGGAGTTGTT GAATGGCCAA TCCGCTCAAG GTTTAATTAC CTGCAAAGAA     1140

GTTCACGAAT GGTTGGAAAC ATGTGGCTCT GTCAAGACT  TCCCATTATT TGAAGCCGTA     1200

TACCAAATCG TTTACAACAA CTACCCAATG AAGAACCTGC CGGACATGAT TGAAGAATTA     1260

GATCTACATG AAGATTAGAT TTATTGGAGA AAGATAACAT ATCATACTTC CCCCACTTTT     1320

TTCGAGGCTC TTCTATATCA TATTCATAAA TTAGCATTAT GTCATTTCTC ATAACTACTT     1380

(2) INFORMATION FOR SEQ ID NO: 2:

(i) SEQUENCE CHARACTERISTICS:
        (A) LENGTH: 2946 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GAATTCGAGC CTGAAGTGCT GATTACCTTC AGGTAGACTT CATCTTGACC CATCAACCCC       60

AGCGTCAATC CTGCAAATAC ACCACCCAGC AGCACTAGGA TGATAGAGAT AATATAGTAC      120

GTGGTAACGC TTGCCTCATC ACCTACGCTA TGGCCGGAAT CGGCAACATC CCTAGAATTG      180

AGTACGTGTG ATCCGGATAA CAACGGCAGT GAATATATCT TCGGTATCGT AAAGATGTGA      240

TATAAGATGA TGTATACCCA ATGAGGAGCG CCTGATCGTG ACCTAGACCT TAGTGGCAAA      300

AACGACATAT CTATTATAGT GGGGAGAGTT TCGTGCAAAT AACAGACGCA GCAGCAAGTA      360

ACTGTGACGA TATCAACTCT TTTTTTATTA TGTAATAAGC AAACAAGCAC GAATGGGGAA      420

AGCCTATGTG CAATCACCAA GGTCGTCCCT TTTTTCCCAT TGCTAATTT  AGAATTTAAA      480

GAAACCAAAA GAATGAAGAA AGAAAACAAA TACTAGCCCT AACCCTGACT TCGTTTCTAT      540

GATAATACCC TGCTTTAATG AACGGTATGC CCTAGGGTAT ATCTCACTCT GTACGTTACA      600

AACTCCGGTT ATTTTATCGG AACATCCGAG CACCCGCGCC TTCCTCAACC CAGGCACCGC      660

CCCAGGTAAC CGTGCGCGAT GAGCTAATCC TGAGCCATCA CCCACCCCAC CCGTTGATGA      720

CAGCAATTCG GGAGGGCGAA AATAAAACTG GAGCAAGGAA TTACCATCAC CGTCACCATC      780

ACCATCATAT CGCCTTAGCC TCTAGCCATA GCCATCATGC AAGCGTGTAT CTTCTAAGAT      840
```

```
TCAGTCATCA TCATTACCGA GTTTGTTTTC CTTCACATGA TGAAGAAGGT TTGAGTATGC      900
TCGAAACAAT AAGACGACGA TGGCTCTGCC ATTGGTTATA TTACGCTTTT GCGGCGAGGT      960
GCCGATGGGT TGCTGAGGGG AAGAGTGTTT AGCTTACGGA CCTATTGCCA TTGTTATTCC     1020
GATTAATCTA TTGTTCAGCA GCTCTTCTCT ACCCTGTCAT TCTAGTATTT TTTTTTTTTT     1080
TTTTTGGTTT TACTTTTTTT TCTTCTTGCC TTTTTTTCTT GTTACTTTTT TTCTAGTTTT     1140
TTTTCCTTCC ACTAAGCTTT TTCCTTGATT TATCCTTGGG TTCTTCTTTC TACTCCTTTA     1200
GATTTTTTTT TTATATATTA ATTTTTAAGT TTATGTATTT TGGTAGATTC AATTCTCTTT     1260
CCCTTTCCTT TTCCTTCGCT CCCCTTCCTT ATCAATGCTT GCTGTCAGAA GATTAACAAG     1320
ATACACATTC CTTAAGCGAA CGCATCCGGT GTTATATACT CGTCGTGCAT ATAAAATTTT     1380
GCCTTCAAGA TCTACTTTCC TAAGAAGATC ATTATTACAA ACACAACTGC ACTCAAAGAT     1440
GACTGCTCAT ACTAATATCA AACAGCACAA ACACTGTCAT GAGGACCATC CTATCAGAAG     1500
ATCGGACTCT GCCGTGTCAA TTGTACATTT GAAACGTGCG CCCTTCAAGG TTACAGTGAT     1560
TGGTTCTGGT AACTGGGGGA CCACCATCGC CAAAGTCATT GCGGAAAACA CAGAATTGCA     1620
TTCCCATATC TTCGAGCCAG AGGTGAGAAT GTGGGTTTTT GATGAAAAGA TCGGCGACGA     1680
AAATCTGACG GATATCATAA ATACAAGACA CCAGAACGTT AAATATCTAC CAATATTGA     1740
CCTGCCCCAT AATCTAGTGG CCGATCCTGA TCTTTTACAC TCCATCAAGG GTGCTGACAT     1800
CCTTGTTTTC AACATCCCTC ATCAATTTTT ACCAAACATA GTCAAACAAT GCAAGGCCA     1860
CGTGGCCCCT CATGTAAGGG CCATCTCGTG TCTAAAAGGG TTCGAGTTGG GCTCCAAGGG     1920
TGTGCAATTG CTATCCTCCT ATGTTACTGA TGAGTTAGGA ATCCAATGTG GCGCACTATC     1980
TGGTGCAAAC TTGGCACCGG AAGTGGCCAA GGAGCATTGG TCCGAAACCA CCGTGGCTTA     2040
CCAACTACCA AAGGATTATC AAGGTGATGG CAAGGATGTA GATCATAAGA TTTTGAAATT     2100
GCTGTTCCAC AGACCTTACT TCCACGTCAA TGTCATCGAT GATGTTGCTG GTATATCCAT     2160
TGCCGGTGCC TTGAAGAACG TCGTGGCACT TGCATGTGGT TTCGTAGAAG GTATGGGATG     2220
GGGTAACAAT GCCTCCGCAG CCATTCAAAG GCTGGGTTTA GGTGAAATTA TCAAGTTCGG     2280
TAGAATGTTT TTCCCAGAAT CCAAAGTCGA GACCTACTAT CAAGAATCCG CTGGTGTTGC     2340
AGATCTGATC ACCACCTGCT CAGGCGGTAG AAACGTCAAG GTTGCCACAT ACATGGCCAA     2400
GACCGGTAAG TCAGCCTTGG AAGCAGAAAA GGAATTGCTT AACGGTCAAT CCGCCCAAGG     2460
GATAATCACA TGCAGAGAAG TTCACGAGTG GCTACAAACA TGTGAGTTGA CCCAAGAATT     2520
CCCAATTATT CGAGGCAGTC TACCAGATAG TCTACAACAA CGTCCGCATG GAAGACCTAC     2580
CGGAGATGAT TGAAGAGCTA GACATCGATG ACGAATAGAC ACTCTCCCCC CCCTCCCCC     2640
TCTGATCTTT CCTGTTGCCT CTTTTTCCCC CAACCAATTT ATCATTATAC ACAAGTTCTA     2700
CAACTACTAC TAGTAACATT ACTACAGTTA TTATAATTTT CTATTCTCTT TTTCTTTAAG     2760
AATCTATCAT TAACGTTAAT TTCTATATAT ACATAACTAC CATTATACAC GCTATTATCG     2820
TTTACATATC ACATCACCGT TAATGAAAGA TACGACACCC TGTACACTAA CACAATTAAA     2880
TAATCGCCAT AACCTTTTCT GTTATCTATA GCCCTTAAAG CTGTTTCTTC GAGCTTTTCA     2940
CTGCAG                                                               2946
```

(2) INFORMATION FOR SEQ ID NO: 3:

(i) SEQUENCE CHARACTERISTICS:
        (A) LENGTH: 3178 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 3:

```
CTGCAGAACT TCGTCTGCTC TGTGCCCATC CTCGCGGTTA GAAAGAAGCT GAATTGTTTC      60
ATGCGCAAGG GCATCAGCGA GTGACCAATA ATCACTGCAC TAATTCCTTT TTAGCAACAC     120
ATACTTATAT ACAGCACCAG ACCTTATGTC TTTTCTCTGC TCCGATACGT TATCCCACCC     180
AACTTTTATT TCAGTTTTGG CAGGGGAAAT TTCACAACCC CGCACGCTAA AAATCGTATT     240
TAAACTTAAA AGAGAACAGC CACAAATAGG GAACTTTGGT CTAAACGAAG GACTCTCCCT     300
CCCTTATCTT GACCGTGCTA TTGCCATCAC TGCTACAAGA CTAAATACGT ACTAATATAT     360
GTTTTCGGTA ACGAGAAGAA GAGCTGCCGG TGCAGCTGCT GCCATGGCCA CAGCCACGGG     420
GACGCTGTAC TGGATGACTA GCCAAGGTGA TAGGCCGTTA GTGCACAATG ACCCGAGCTA     480
CATGGTGCAA TTCCCCACCG CCGCTCCACC GGCAGGTCTC TAGACGAGAC CTGCTGGACC     540
GTCTGGACAA GACGCATCAA TTCGACGTGT TGATCATCGG TGGCGGGGCC ACGGGGACAG     600
GATGTGCCCT AGATGCTGCG ACCAGGGGAC TCAATGTGGC CCTTGTTGAA AAGGGGGATT     660
TTGCCTCGGG AACGTCGTCC AAATCTACCA AGATGATTCA CGGTGGGGTG CGGTACTTAG     720
AGAAGGCCTT CTGGGAGTTC TCCAAGGCAC AACTGGATCT GGTCATCGAG GCACTCAACG     780
AGCGTAAACA TCTTATCAAC ACTGCCCCTC ACCTGTGCAC GGTGCTACCA ATTCTGATCC     840
CCATCTACAG CACCTGGCAG GTCCCGTACA TCTATATGGG CTGTAAATTC TACGATTTCT     900
TTGGCGGTTC CCAAAACTTG AAAAAATCAT ACCTACTGTC CAAATCCGCC ACCGTGGAGA     960
AGGCTCCCAT GCTTACCACA GACAATTTAA AGGCCTCGCT TGTGTACCAT GATGGGTCCT    1020
TTAACGACTC GCGTTTGAAC GCCACTTTAG CCATCACGGG TGTGGAGAAC GGCGCTACCG    1080
TCTTGATCTA TGTCGAGGTA CAAAAATTGA TCAAAGACCC AACTTCTGGT AAGGTTATCG    1140
GTGCCGAGGC CCGGGACGTT GAGACTAATG AGCTTGTCAG AATCAACGCT AAATGTGTGG    1200
TCAATGCCAC GGGCCCATAC AGTGACGCCA TTTTGCAAAT GGACCGCAAC CCATCCGGTC    1260
TGCCGGACTC CCCGCTAAAC GACAACTCCA AGATCAAGTC GACTTTCAAT CAAATCTCCG    1320
TCATGGACCC GAAAATGGTC ATCCCATCTA TTGGCGTTCA CATCGTATTG CCCTCTTTTT    1380
ACTCCCCGAA GGATATGGGT TGTTGGACG TCAGAACCTC TGATGGCAGA GTGATGTTCT    1440
TTTTACCTTG GCAGGGCAAA GTCCTTGCCG GCACCACAGA CATCCCACTA AGCAAGTCC    1500
CAGAAAACCC TATGCCTACA GAGGCTGATA TTCAAGATAT CTTGAAAGAA CTACAGCACT    1560
ATATCGAATT CCCCGTGAAA AGAGAAGACG TGCTAAGTGC ATGGGCTGGT GTCAGACCTT    1620
TGGTCAGAGA TCCACGTACA ATCCCCGCAG ACGGGAAGAA GGGCTCTGCC ACTCAGGGCG    1680
TGGTAAGATC CCACTTCTTG TTCACTTCGG ATAATGGCCT AATTACTATT GCAGGTGGTA    1740
AATGGACTAC TTACAGACAA ATGGCTGAGG AAACAGTCGA CAAAGTTGTC GAAGTTGGCG    1800
GATTCCACAA CCTGAAACCT TGTCACACAA GAGATATTAA GCTTGCTGGT GCAGAAGAAT    1860
GGACGCAAAA CTATGTGGCT TTATTGGCTC AAAACTACCA TTTATCATCA AAAATGTCCA    1920
ACTACTTGGT TCAAAACTAC GGAACCCGTT CCTCTATCAT TTGCGAATTT TCAAAGAAT    1980
CCATGGAAAA TAAACTGCCT TTGTCCTTAG CCGACAAGGA AATAACGTA ATCTACTCTA    2040
GCGAGGAGAA CAACTTGGTC AATTTTGATA CTTTCAGATA TCCATTCACA ATCGGTGAGT    2100
TAAAGTATTC CATGCAGTAC GAATATTGTA GAACTCCCTT GGACTTCCTT TTAAGAAGAA    2160
CAAGATTCGC CTTCTTGGAC GCCAAGGAAG CTTTGAATGC CGTGCATGCC ACCGTCAAAG    2220
```

-continued

```
TTATGGGTGA TGAGTTCAAT TGGTCGGAGA AAAAGAGGCA GTGGGAACTT GAAAAAACTG      2280

TGAACTTCAT CCAAGGACGT TTCGGTGTCT AAATCGATCA TGATAGTTAA GGGTGACAAA      2340

GATAACATTC ACAAGAGTAA TAATAATGGT AATGATGATA ATAATAATAA TGATAGTAAT      2400

AACAATAATA ATAATGGTGG TAATGGCAAT GAAATCGCTA TTATTACCTA TTTTCCTTAA      2460

TGGAAGAGTT AAAGTAAACT AAAAAAACTA CAAAAATATA TGAAGAAAAA AAAAAAAAGA      2520

GGTAATAGAC TCTACTACTA CAATTGATCT TCAAATTATG ACCTTCCTAG TGTTTATATT      2580

CTATTTCCAA TACATAATAT AATCTATATA ATCATTGCTG GTAGACTTCC GTTTTAATAT      2640

CGTTTTAATT ATCCCCTTTA TCTCTAGTCT AGTTTTATCA TAAAATATAG AAACACTAAA      2700

TAATATTCTT CAAACGGTCC TGGTGCATAC GCAATACATA TTTATGGTGC AAAAAAAAAA      2760

ATGGAAAATT TTGCTAGTCA TAAACCCTTT CATAAAACAA TACGTAGACA TCGCTACTTG      2820

AAATTTTCAA GTTTTTATCA GATCCATGTT TCCTATCTGC CTTGACAACC TCATCGTCGA      2880

AATAGTACCA TTTAGAACGC CCAATATTCA CATTGTGTTC AAGGTCTTTA TTCACCAGTG      2940

ACGTGTAATG GCCATGATTA ATGTGCCTGT ATGGTTAACC ACTCCAAATA GCTTATATTT      3000

CATAGTGTCA TTGTTTTTCA ATATAATGTT TAGTATCAAT GGATATGTTA CGACGGTGTT      3060

ATTTTTCTTG GTCAAATCGT AATAAAATCT CGATAAATGG ATGACTAAGA TTTTTGGTAA      3120

AGTTACAAAA TTTATCGTTT TCACTGTTGT CAATTTTTTG TTCTTGTAAT CACTCGAG       3178
```

(2) INFORMATION FOR SEQ ID NO: 4:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
ATGAAACGTT TCAATGTTTT AAAATATATC AGAACAACAA AAGCAAATAT ACAAACCATC        60

GCAATGCCTT TGACCACAAA ACCTTTATCT TTGAAAATCA ACGCCGCTCT ATTCGATGTT       120

GACGGTACCA TCATCATCTC TCAACCAGCC ATTGCTGCTT TCTGGAGAGA TTTCGGTAAA       180

GACAAGCCTT ACTTCGATGC CGAACACGTT ATTCACATCT CTCACGGTTG GAGAACTTAC       240

GATGCCATTG CCAAGTTCGC TCCAGACTTT GCTGATGAAG AATACGTTAA CAAGCTAGAA       300

GGTGAAATCC CAGAAAAGTA CGGTGAACAC TCCATCGAAG TTCCAGGTGC TGTCAAGTTG       360

TGTAATGCTT TGAACGCCTT GCCAAAGGAA AAATGGGCTG TCGCCACCTC TGGTACCCGT       420

GACATGGCCA AGAAATGGTT CGACATTTTG AAGATCAAGA GACCAGAATA CTTCATCACC       480

GCCAATGATG TCAAGCAAGG TAAGCCTCAC CCAGAACCAT ACTTAAAGGG TAGAAACGGT       540

TTGGGTTTCC CAATTAATGA ACAAGACCCA TCCAAATCTA AGGTTGTTGT CTTTGAAGAC       600

GCACCAGCTG GTATTGCTGC TGGTAAGGCT GCTGGCTGTA AAATCGTTGG TATTGCTACC       660

ACTTTCGATT TGGACTTCTT GAAGGAAAAG GGTTGTGACA TCATTGTCAA GAACCACGAA       720

TCTATCAGAG TCGGTGAATA CAACGCTGAA ACCGATGAAG TCGAATTGAT CTTTGATGAC       780

TACTTATACG CTAAGGATGA CTTGTTGAAA TGGTAA                                 816
```

(2) INFORMATION FOR SEQ ID NO: 5:

(i) SEQUENCE CHARACTERISTICS:
        (A) LENGTH: 753 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

```
ATGGGATTGA CTACTAAACC TCTATCTTTG AAAGTTAACG CCGCTTTGTT CGACGTCGAC    60

GGTACCATTA TCATCTCTCA ACCAGCCATT GCTGCATTCT GGAGGGATTT CGGTAAGGAC   120

AAACCTTATT TCGATGCTGA ACACGTTATC CAAGTCTCGC ATGGTTGGAG AACGTTTGAT   180

GCCATTGCTA AGTTCGCTCC AGACTTTGCC AATGAAGAGT ATGTTAACAA ATTAGAAGCT   240

GAAATTCCGG TCAAGTACGG TGAAAAATCC ATTGAAGTCC CAGGTGCAGT TAAGCTGTGC   300

AACGCTTTGA ACGCTCTACC AAAAGAGAAA TGGGCTGTGG CAACTTCCGG TACCCGTGAT   360

ATGGCACAAA ATGGTTCGA GCATCTGGGA ATCAGGAGAC CAAAGTACTT CATTACCGCT   420

AATGATGTCA ACAGGGTAA GCCTCATCCA GAACCATATC TGAAGGGCAG GAATGGCTTA   480

GGATATCCGA TCAATGAGCA AGACCCTTCC AAATCTAAGG TAGTAGTATT TGAAGACGCT   540

CCAGCAGGTA TTGCCGCCGG AAAAGCCGCC GGTTGTAAGA TCATTGGTAT TGCCACTACT   600

TTCGACTTGG ACTTCCTAAA GGAAAAAGGC TGTGACATCA TTGTCAAAAA CCACGAATCC   660

ATCAGAGTTG GCGGCTACAA TGCCGAAACA GACGAAGTTG AATTCATTTT TGACGACTAC   720

TTATATGCTA AGGACGATCT GTTGAAATGG TAA                                753
```

(2) INFORMATION FOR SEQ ID NO: 6:

(i) SEQUENCE CHARACTERISTICS:
        (A) LENGTH: 2520 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
TGTATTGGCC ACGATAACCA CCCTTTGTAT ACTGTTTTTG TTTTTCACAT GGTAAATAAC    60

GACTTTTATT AAACAACGTA TGTAAAAACA TAACAAGAAT CTACCCATAC AGGCCATTTC   120

GTAATTCTTC TCTTCTAATT GGAGTAAAAC CATCAATTAA AGGGTGTGGA GTAGCATAGT   180

GAGGGGCTGA CTGCATTGAC AAAAAAATTG AAAAAAAAAA AGGAAAAGGA AAGGAAAAAA   240

AGACAGCCAA GACTTTTAGA ACGGATAAGG TGTAATAAAA TGTGGGGGGA TGCCTGTTCT   300

CGAACCATAT AAAATATACC ATGTGGTTTG AGTTGTGGCC GGAACTATAC AAATAGTTAT   360

ATGTTTCCCT CTCTCTTCCG ACTTGTAGTA TTCTCCAAAC GTTACATATT CCGATCAAGC   420

CAGCGCCTTT ACACTAGTTT AAAACAAGAA CAGAGCCGTA TGTCCAAAAT AATGGAAGAT   480

TTACGAAGTG ACTACGTCCC GCTTATCGCC AGTATTGATG TAGGAACGAC CTCATCCAGA   540

TGCATTCTGT TCAACAGATG GGGCCAGGAC GTTTCAAAAC ACCAAATTGA ATATTCAACT   600

TCAGCATCGA AGGGCAAGAT TGGGGTGTCT GGCCTAAGGA GACCCTCTAC AGCCCCAGCT   660

CGTGAAACAC CAAACGCCGG TGACATCAAA ACCAGCGGAA AGCCCATCTT TTCTGCAGAA   720

GGCTATGCCA TTCAAGAAAC CAAATTCCTA AAAATCGAGG AATTGGACTT GGACTTCCAT   780

AACGAACCCA CGTTGAAGTT CCCCAAACCG GGTTGGGTTG AGTGCCATCC GCAGAAATTA   840

CTGGTGAACG TCGTCCAATG CCTTGCCTCA AGTTTGCTCT CTCTGCAGAC TATCAACAGC   900

GAACGTGTAG CAAACGGTCT CCCACCTTAC AAGGTAATAT GCATGGGTAT AGCAAACATG   960
```

-continued

```
AGAGAAACCA CAATTCTGTG GTCCCGCCGC ACAGGAAAAC CAATTGTTAA CTACGGTATT    1020

GTTTGGAACG ACACCAGAAC GATCAAAATC GTTAGAGACA AATGGCAAAA CACTAGCGTC    1080

GATAGGCAAC TGCAGCTTAG ACAGAAGACT GGATTGCCAT TGCTCTCCAC GTATTTCTCC    1140

TGTTCCAAGC TGCGCTGGTT CCTCGACAAT GAGCCTCTGT GTACCAAGGC GTATGAGGAG    1200

AACGACCTGA TGTTCGGCAC TGTGGACACA TGGCTGATTT ACCAATTAAC TAAACAAAAG    1260

GCGTTCGTTT CTGACGTAAC CAACGCTTCC AGAACTGGAT TTATGAACCT CTCCACTTTA    1320

AAGTACGACA ACGAGTTGCT GGAATTTTGG GGTATTGACA AGAACCTGAT TCACATGCCC    1380

GAAATTGTGT CCTCATCTCA ATACTACGGT GACTTTGGCA TTCCTGATTG GATAATGGAA    1440

AAGCTACACG ATTCGCCAAA AACAGTACTG CGAGATCTAG TCAAGAGAAA CCTGCCCATA    1500

CAGGGCTGTC TGGGCGACCA AAGCGCATCC ATGGTGGGGC AACTCGCTTA CAAACCCGGT    1560

GCTGCAAAAT GTACTTATGG TACCGGTTGC TTTTTACTGT ACAATACGGG GACCAAAAAA    1620

TTGATCTCCC AACATGGCGC ACTGACGACT CTAGCATTTT GGTTCCCACA TTTGCAAGAG    1680

TACGGTGGCC AAAAACCAGA ATTGAGCAAG CCACATTTTG CATTAGAGGG TTCCGTCGCT    1740

GTGGCTGGTG CTGTGGTCCA ATGGCTACGT GATAATTTAC GATTGATCGA TAAATCAGAG    1800

GATGTCGGAC CGATTGCATC TACGGTTCCT GATTCTGGTG GCGTAGTTTT CGTCCCCGCA    1860

TTTAGTGGCC TATTCGCTCC CTATTGGGAC CCAGATGCCA GAGCCACCAT AATGGGGATG    1920

TCTCAATTCA CTACTGCCTC CCACATCGCC AGAGCTGCCG TGGAAGGTGT TTGCTTTCAA    1980

GCCAGGGCTA TCTTGAAGGC AATGAGTTCT GACGCGTTTG GTGAAGGTTC CAAAGACAGG    2040

GACTTTTTAG AGGAAATTTC CGACGTCACA TATGAAAAGT CGCCCCTGTC GGTTCTGGCA    2100

GTGGATGGCG GGATGTCGAG GTCTAATGAA GTCATGCAAA TTCAAGCCGA TATCCTAGGT    2160

CCCTGTGTCA AAGTCAGAAG GTCTCCGACA GCGGAATGTA CCGCATTGGG GGCAGCCATT    2220

GCAGCCAATA TGGCTTTCAA GGATGTGAAC GAGCGCCCAT TATGGAAGGA CCTACACGAT    2280

GTTAAGAAAT GGGTCTTTTA CAATGGAATG GAGAAAAACG AACAAATATC ACCAGAGGCT    2340

CATCCAAACC TTAAGATATT CAGAAGTGAA TCCGACGATG CTGAAAGGAG AAAGCATTGG    2400

AAGTATTGGG AAGTTGCCGT GGAAAGATCC AAAGGTTGGC TGAAGGACAT AGAAGGTGAA    2460

CACGAACAGG TTCTAGAAAA CTTCCAATAA CAACATAAAT AATTTCTATT AACAATGTAA    2520
```

(2) INFORMATION FOR SEQ ID NO: 7:

(i) SEQUENCE CHARACTERISTICS:
        (A) LENGTH: 391 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 7:

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Ile Asn Gly Glu
65                  70                  75                  80
```

```
Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

(2) INFORMATION FOR SEQ ID NO: 8:

(i) SEQUENCE CHARACTERISTICS:
        (A) LENGTH: 384 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 8:

Met Thr Ala His Thr Asn Ile Lys Gln His Lys His Cys His Glu Asp
1               5                   10                  15

His Pro Ile Arg Arg Ser Asp Ser Ala Val Ser Ile Val His Leu Lys
            20                  25                  30
```

```
Arg Ala Pro Phe Lys Val Thr Val Ile Gly Ser Gly Asn Trp Gly Thr
            35                  40                  45

Thr Ile Ala Lys Val Ile Ala Glu Asn Thr Glu Leu His Ser His Ile
 50                  55                  60

Phe Glu Pro Glu Val Arg Met Trp Val Phe Asp Glu Lys Ile Gly Asp
 65                  70                  75                  80

Glu Asn Leu Thr Asp Ile Ile Asn Thr Arg His Gln Asn Val Lys Tyr
                85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
            115                 120                 125

Gln Phe Leu Pro Asn Ile Val Lys Gln Leu Gln Gly His Val Ala Pro
130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
            195                 200                 205

Gly Asp Gly Lys Asp Val Asp His Lys Ile Leu Lys Leu Leu Phe His
            210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
            275                 280                 285

Lys Val Glu Thr Tyr Tyr Gln Glu Ser Ala Gly Val Ala Asp Leu Ile
            290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350

Gln Thr Cys Glu Leu Thr Gln Glu Phe Pro Ile Ile Arg Gly Ser Leu
            355                 360                 365

Pro Asp Ser Leu Gln Gln Arg Pro His Gly Arg Pro Thr Gly Asp Asp
            370                 375                 380

(2) INFORMATION FOR SEQ ID NO: 9:

(i) SEQUENCE CHARACTERISTICS:
        (A) LENGTH: 614 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 9:
```

```
Met Thr Arg Ala Thr Trp Cys Asn Ser Pro Pro Leu His Arg Gln
1               5                   10                  15

Val Ser Arg Arg Asp Leu Leu Asp Arg Leu Asp Lys Thr His Gln Phe
            20                  25                  30

Asp Val Leu Ile Ile Gly Gly Gly Ala Thr Gly Thr Gly Cys Ala Leu
            35                  40                  45

Asp Ala Ala Thr Arg Gly Leu Asn Val Ala Leu Val Glu Lys Gly Asp
        50                  55                  60

Phe Ala Ser Gly Thr Ser Ser Lys Ser Thr Lys Met Ile His Gly Gly
65                  70                  75                  80

Val Arg Tyr Leu Glu Lys Ala Phe Trp Glu Phe Ser Lys Ala Gln Leu
                85                  90                  95

Asp Leu Val Ile Glu Ala Leu Asn Glu Arg Lys His Leu Ile Asn Thr
                100                 105                 110

Ala Pro His Leu Cys Thr Val Leu Pro Ile Leu Ile Pro Ile Tyr Ser
            115                 120                 125

Thr Trp Gln Val Pro Tyr Ile Tyr Met Gly Cys Lys Phe Tyr Asp Phe
        130                 135                 140

Phe Gly Gly Ser Gln Asn Leu Lys Lys Ser Tyr Leu Leu Ser Lys Ser
145                 150                 155                 160

Ala Thr Val Glu Lys Ala Pro Met Leu Thr Thr Asp Asn Leu Lys Ala
                165                 170                 175

Ser Leu Val Tyr His Asp Gly Ser Phe Asn Asp Ser Arg Leu Asn Ala
            180                 185                 190

Thr Leu Ala Ile Thr Gly Val Glu Asn Gly Ala Thr Val Leu Ile Tyr
        195                 200                 205

Val Glu Val Gln Lys Leu Ile Lys Asp Pro Thr Ser Gly Lys Val Ile
        210                 215                 220

Gly Ala Glu Ala Arg Asp Val Glu Thr Asn Glu Leu Val Arg Ile Asn
225                 230                 235                 240

Ala Lys Cys Val Val Asn Ala Thr Gly Pro Tyr Ser Asp Ala Ile Leu
            245                 250                 255

Gln Met Asp Arg Asn Pro Ser Gly Leu Pro Asp Ser Pro Leu Asn Asp
            260                 265                 270

Asn Ser Lys Ile Lys Ser Thr Phe Asn Gln Ile Ser Val Met Asp Pro
            275                 280                 285

Lys Met Val Ile Pro Ser Ile Gly Val His Ile Val Leu Pro Ser Phe
        290                 295                 300

Tyr Ser Pro Lys Asp Met Gly Leu Leu Asp Val Arg Thr Ser Asp Gly
305                 310                 315                 320

Arg Val Met Phe Phe Leu Pro Trp Gln Gly Lys Val Leu Ala Gly Thr
                325                 330                 335

Thr Asp Ile Pro Leu Lys Gln Val Pro Glu Asn Pro Met Pro Thr Glu
            340                 345                 350

Ala Asp Ile Gln Asp Ile Leu Lys Glu Leu Gln His Tyr Ile Glu Phe
            355                 360                 365

Pro Val Lys Arg Glu Asp Val Leu Ser Ala Trp Ala Gly Val Arg Pro
        370                 375                 380

Leu Val Arg Asp Pro Arg Thr Ile Pro Ala Asp Gly Lys Lys Gly Ser
385                 390                 395                 400

Ala Thr Gln Gly Val Val Arg Ser His Phe Leu Phe Thr Ser Asp Asn
                405                 410                 415
```

-continued

```
Gly Leu Ile Thr Ile Ala Gly Gly Lys Trp Thr Thr Tyr Arg Gln Met
                420             425             430
Ala Glu Glu Thr Val Asp Lys Val Glu Val Gly Gly Phe His Asn
        435             440             445
Leu Lys Pro Cys His Thr Arg Asp Ile Lys Leu Ala Gly Ala Glu Glu
450             455             460
Trp Thr Gln Asn Tyr Val Ala Leu Leu Ala Gln Asn Tyr His Leu Ser
465             470             475             480
Ser Lys Met Ser Asn Tyr Leu Val Gln Asn Tyr Gly Thr Arg Ser Ser
            485             490             495
Ile Ile Cys Glu Phe Phe Lys Glu Ser Met Glu Asn Lys Leu Pro Leu
                500             505             510
Ser Leu Ala Asp Lys Glu Asn Asn Val Ile Tyr Ser Ser Glu Glu Asn
            515             520             525
Asn Leu Val Asn Phe Asp Thr Phe Arg Tyr Pro Phe Thr Ile Gly Glu
530             535             540
Leu Lys Tyr Ser Met Gln Tyr Glu Tyr Cys Arg Thr Pro Leu Asp Phe
545             550             555             560
Leu Leu Arg Arg Thr Arg Phe Ala Phe Leu Asp Ala Lys Glu Ala Leu
                565             570             575
Asn Ala Val His Ala Thr Val Lys Val Met Gly Asp Glu Phe Asn Trp
            580             585             590
Ser Glu Lys Lys Arg Gln Trp Glu Leu Glu Lys Thr Val Asn Phe Ile
            595             600             605
Gln Gly Arg Phe Gly Val
        610

(2) INFORMATION FOR SEQ ID NO: 10:

(i) SEQUENCE CHARACTERISTICS:
        (A) LENGTH: 339 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 10:

Met Asn Gln Arg Asn Ala Ser Met Thr Val Ile Gly Ala Gly Ser Tyr
1               5               10              15
Gly Thr Ala Leu Ala Ile Thr Leu Ala Arg Asn Gly His Glu Val Val
            20              25              30
Leu Trp Gly His Asp Pro Glu His Ile Ala Thr Leu Glu Arg Asp Arg
        35              40              45
Cys Asn Ala Ala Phe Leu Pro Asp Val Pro Phe Pro Asp Thr Leu His
    50              55              60
Leu Glu Ser Asp Leu Ala Thr Ala Leu Ala Ala Ser Arg Asn Ile Leu
65              70              75              80
Val Val Val Pro Ser His Val Phe Gly Glu Val Leu Arg Gln Ile Lys
                85              90              95
Pro Leu Met Arg Pro Asp Ala Arg Leu Val Trp Ala Thr Lys Gly Leu
            100             105             110
Glu Ala Glu Thr Gly Arg Leu Leu Gln Asp Val Ala Arg Glu Ala Leu
        115             120             125
Gly Asp Gln Ile Pro Leu Ala Val Ile Ser Gly Pro Thr Phe Ala Lys
    130             135             140
```

-continued

```
Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu His Cys Gly Lys Ser
                165                 170                 175

Phe Arg Val Tyr Ser Asn Pro Asp Phe Ile Gly Val Gln Leu Gly Gly
                180                 185                 190

Ala Val Lys Asn Val Ile Ala Ile Gly Ala Gly Met Ser Asp Gly Ile
            195                 200                 205

Gly Phe Gly Ala Asn Ala Arg Thr Ala Leu Ile Thr Arg Gly Leu Ala
        210                 215                 220

Glu Met Ser Arg Leu Gly Ala Ala Leu Gly Ala Asp Pro Ala Thr Phe
225                 230                 235                 240

Met Gly Met Ala Gly Leu Gly Asp Leu Val Leu Thr Cys Thr Asp Asn
                245                 250                 255

Gln Ser Arg Asn Arg Arg Phe Gly Met Met Leu Gly Gln Gly Met Asp
            260                 265                 270

Val Gln Ser Ala Gln Glu Lys Ile Gly Gln Val Val Glu Gly Tyr Arg
        275                 280                 285

Asn Thr Lys Glu Val Arg Glu Leu Ala His Arg Phe Gly Val Glu Met
290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
                325                 330                 335

Ser Ser His
```

(2) INFORMATION FOR SEQ ID NO: 11:

(i) SEQUENCE CHARACTERISTICS:
        (A) LENGTH: 501 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 11:

```
Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
                100                 105                 110

Lys Arg Thr Ser Leu Pro Gly Ser Thr Gly Leu Arg Phe Gly Ala Asn
            115                 120                 125

Ser Val Leu Lys Pro Glu Ile Lys Arg Gly Phe Glu Tyr Ser Asp Cys
        130                 135                 140

Trp Val Asp Asp Ala Arg Leu Val Leu Ala Asn Ala Gln Met Val Val
```

-continued

```
             145                 150                 155                 160
    Arg Lys Gly Gly Glu Val Leu Thr Arg Thr Arg Ala Thr Ser Ala Arg
                    165                 170                 175

Arg Glu Asn Gly Leu Trp Ile Val Glu Ala Glu Asp Ile Asp Thr Gly
                    180                 185                 190

Lys Lys Tyr Ser Trp Gln Ala Arg Gly Leu Val Asn Ala Thr Gly Pro
                    195                 200                 205

Trp Val Lys Gln Phe Phe Asp Asp Gly Met His Leu Pro Ser Pro Tyr
                    210                 215                 220

Gly Ile Arg Leu Ile Lys Gly Ser His Ile Val Val Pro Arg Val His
    225                 230                 235                 240

Thr Gln Lys Gln Ala Tyr Ile Leu Gln Asn Glu Asp Lys Arg Ile Val
                    245                 250                 255

Phe Val Ile Pro Trp Met Asp Glu Phe Ser Ile Ile Gly Thr Thr Asp
                    260                 265                 270

Val Glu Tyr Lys Gly Asp Pro Lys Ala Val Lys Ile Glu Glu Ser Glu
                    275                 280                 285

Ile Asn Tyr Leu Leu Asn Val Tyr Asn Thr His Phe Lys Lys Gln Leu
    290                 295                 300

Ser Arg Asp Asp Ile Val Trp Thr Tyr Ser Gly Val Arg Pro Leu Cys
    305                 310                 315                 320

Asp Asp Glu Ser Asp Ser Pro Gln Ala Ile Thr Arg Asp Tyr Thr Leu
                    325                 330                 335

Asp Ile His Asp Glu Asn Gly Lys Ala Pro Leu Leu Ser Val Phe Gly
                    340                 345                 350

Gly Lys Leu Thr Thr Tyr Arg Lys Leu Ala Glu His Ala Leu Glu Lys
                    355                 360                 365

Leu Thr Pro Tyr Tyr Gln Gly Ile Gly Pro Ala Trp Thr Lys Glu Ser
                    370                 375                 380

Val Leu Pro Gly Gly Ala Ile Glu Gly Asp Arg Asp Asp Tyr Ala Ala
    385                 390                 395                 400

Arg Leu Arg Arg Arg Tyr Pro Phe Leu Thr Glu Ser Leu Ala Arg His
                    405                 410                 415

Tyr Ala Arg Thr Tyr Gly Ser Asn Ser Glu Leu Leu Leu Gly Asn Ala
                    420                 425                 430

Gly Thr Val Ser Asp Leu Gly Glu Asp Phe Gly His Glu Phe Tyr Glu
                    435                 440                 445

Ala Glu Leu Lys Tyr Leu Val Asp His Glu Trp Val Arg Arg Ala Asp
                    450                 455                 460

Asp Ala Leu Trp Arg Arg Thr Lys Gln Gly Met Trp Leu Asn Ala Asp
    465                 470                 475                 480

Gln Gln Ser Arg Val Ser Gln Trp Leu Val Glu Tyr Thr Gln Gln Arg
                    485                 490                 495

Leu Ser Leu Ala Ser
                    500

(2) INFORMATION FOR SEQ ID NO: 12:

(i) SEQUENCE CHARACTERISTICS:
        (A) LENGTH: 542 amino acids
        (B) TYPE: amino acid
        (C) STRANDEDNESS: unknown
        (D) TOPOLOGY: unknown (ii) MOLECULE TYPE: protein
```

(xi) SEQUENCE DESCRIPTION: SEQ ID NO: 12:

Met Lys Thr Arg Asp Ser Gln Ser Ser Asp Val Ile Ile Ile Gly Gly
1               5                   10                  15

Gly Ala Thr Gly Ala Gly Ile Ala Arg Asp Cys Ala Leu Arg Gly Leu
            20                  25                  30

Arg Val Ile Leu Val Glu Arg His Asp Ile Ala Thr Gly Ala Thr Gly
        35                  40                  45

Arg Asn His Gly Leu Leu His Ser Gly Ala Arg Tyr Ala Val Thr Asp
    50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
            100                 105                 110

Glu Ala Gly Ile Ser Ala Glu Ala Ile Asp Pro Gln Gln Ala Arg Ile
        115                 120                 125

Ile Glu Pro Ala Val Asn Pro Ala Leu Ile Gly Ala Val Lys Val Pro
    130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Val Asn Ala
        195                 200                 205

Ala Gly Ile Trp Gly Gln His Ile Ala Glu Tyr Ala Asp Leu Arg Ile
    210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asp Asn Arg Val Thr Ala Glu Glu Val
        275                 280                 285

Asp Ile Leu Leu Arg Glu Gly Glu Lys Leu Ala Pro Val Met Ala Lys
    290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Leu Ser Arg Gly Ile Val Leu Leu
                325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
        355                 360                 365

Val Cys Arg Lys Leu Gly Asn Thr Arg Pro Cys Thr Thr Ala Asp Leu
    370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

```
Asp Arg Thr Pro Ala Trp Leu Ser Glu Gly Arg Leu His Arg Ser Leu
            420                 425                 430

Val Cys Glu Cys Glu Ala Val Thr Ala Gly Glu Val Gln Tyr Ala Val
            435                 440                 445

Glu Asn Leu Asn Val Asn Ser Leu Leu Asp Leu Arg Arg Arg Thr Arg
            450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
            515                 520                 525

Gln Gly Leu Cys Gly Leu Glu Lys Glu Gln Lys Asp Ala Leu
            530                 535                 540

(2) INFORMATION FOR SEQ ID NO: 13:

(i) SEQUENCE CHARACTERISTICS:
        (A) LENGTH: 250 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 13:

Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
65              70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
            115                 120                 125

Leu Gly Ile Arg Arg Pro Lys Tyr Phe Ile Thr Ala Asn Asp Val Lys
            130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
            195                 200                 205

Lys Gly Cys Asp Ile Ile Val Lys Asn His Glu Ser Ile Arg Val Gly
210                 215                 220
```

```
Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250
```

(2) INFORMATION FOR SEQ ID NO: 14:

(i) SEQUENCE CHARACTERISTICS:
        (A) LENGTH: 271 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 14:

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
                20                  25                  30

Ile Asn Ala Ala Leu Phe Asp Val Asp Gly Thr Ile Ile Ile Ser Gln
                35                  40                  45

Pro Ala Ile Ala Ala Phe Trp Arg Asp Phe Gly Lys Asp Lys Pro Tyr
50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
                100                 105                 110

Glu Val Pro Gly Ala Val Lys Leu Cys Asn Ala Leu Asn Ala Leu Pro
                115                 120                 125

Lys Glu Lys Trp Ala Val Ala Thr Ser Gly Thr Arg Asp Met Ala Lys
                130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
                180                 185                 190

Ser Lys Val Val Val Phe Glu Asp Ala Pro Ala Gly Ile Ala Ala Gly
                195                 200                 205

Lys Ala Ala Gly Cys Lys Ile Val Gly Ile Ala Thr Thr Phe Asp Leu
                210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
                260                 265                 270
```

(2) INFORMATION FOR SEQ ID NO: 15:

(i) SEQUENCE CHARACTERISTICS:
        (A) LENGTH: 709 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 15:

```
Met Phe Pro Ser Leu Phe Arg Leu Val Val Phe Ser Lys Arg Tyr Ile
1               5                   10                  15

Phe Arg Ser Ser Gln Arg Leu Tyr Thr Ser Leu Lys Gln Glu Gln Ser
                20                  25                  30

Arg Met Ser Lys Ile Met Glu Asp Leu Arg Ser Asp Tyr Val Pro Leu
                35                  40                  45

Ile Ala Ser Ile Asp Val Gly Thr Thr Ser Ser Arg Cys Ile Leu Phe
50                          55                  60

Asn Arg Trp Gly Gln Asp Val Ser Lys His Gln Ile Glu Tyr Ser Thr
65                      70                  75                  80

Ser Ala Ser Lys Gly Lys Ile Gly Val Ser Gly Leu Arg Arg Pro Ser
                    85                  90                  95

Thr Ala Pro Ala Arg Glu Thr Pro Asn Ala Gly Asp Ile Lys Thr Ser
                100                 105                 110

Gly Lys Pro Ile Phe Ser Ala Glu Gly Tyr Ala Ile Gln Glu Thr Lys
                115                 120                 125

Phe Leu Lys Ile Glu Glu Leu Asp Leu Asp Phe His Asn Glu Pro Thr
130                 135                 140

Leu Lys Phe Pro Lys Pro Gly Trp Val Glu Cys His Pro Gln Lys Leu
145                 150                 155                 160

Leu Val Asn Val Val Gln Cys Leu Ala Ser Leu Leu Ser Leu Gln
                    165                 170                 175

Thr Ile Asn Ser Glu Arg Val Ala Asn Gly Leu Pro Pro Tyr Lys Val
                180                 185                 190

Ile Cys Met Gly Ile Ala Asn Met Arg Glu Thr Thr Ile Leu Trp Ser
                195                 200                 205

Arg Arg Thr Gly Lys Pro Ile Val Asn Tyr Gly Ile Val Trp Asn Asp
                210                 215                 220

Thr Arg Thr Ile Lys Ile Val Arg Asp Lys Trp Gln Asn Thr Ser Val
225                 230                 235                 240

Asp Arg Gln Leu Gln Leu Arg Gln Lys Thr Gly Leu Pro Leu Leu Ser
                245                 250                 255

Thr Tyr Phe Ser Cys Ser Lys Leu Arg Trp Phe Leu Asp Asn Glu Pro
                260                 265                 270

Leu Cys Thr Lys Ala Tyr Glu Glu Asn Asp Leu Met Phe Gly Thr Val
                275                 280                 285

Asp Thr Trp Leu Ile Tyr Gln Leu Thr Lys Gln Lys Ala Phe Val Ser
                290                 295                 300

Asp Val Thr Asn Ala Ser Arg Thr Gly Phe Met Asn Leu Ser Thr Leu
305                 310                 315                 320

Lys Tyr Asp Asn Glu Leu Leu Glu Phe Trp Gly Ile Asp Lys Asn Leu
                    325                 330                 335

Ile His Met Pro Glu Ile Val Ser Ser Gln Tyr Tyr Gly Asp Phe
                340                 345                 350

Gly Ile Pro Asp Trp Ile Met Glu Lys Leu His Asp Ser Pro Lys Thr
                355                 360                 365

Val Leu Arg Asp Leu Val Lys Arg Asn Leu Pro Ile Gln Gly Cys Leu
                370                 375                 380

Gly Asp Gln Ser Ala Ser Met Val Gly Gln Leu Ala Tyr Lys Pro Gly
385                 390                 395                 400
```

```
Ala Ala Lys Cys Thr Tyr Gly Thr Gly Cys Phe Leu Leu Tyr Asn Thr
            405                 410                 415
Gly Thr Lys Lys Leu Ile Ser Gln His Gly Ala Leu Thr Thr Leu Ala
            420                 425                 430
Phe Trp Phe Pro His Leu Gln Glu Tyr Gly Gly Gln Lys Pro Glu Leu
            435                 440                 445
Ser Lys Pro His Phe Ala Leu Glu Gly Ser Val Ala Val Ala Gly Ala
            450                 455                 460
Val Val Gln Trp Leu Arg Asp Asn Leu Arg Leu Ile Asp Lys Ser Glu
465                 470                 475                 480
Asp Val Gly Pro Ile Ala Ser Thr Val Pro Asp Ser Gly Gly Val Val
                    485                 490                 495
Phe Val Pro Ala Phe Ser Gly Leu Phe Ala Pro Tyr Trp Asp Pro Asp
                500                 505                 510
Ala Arg Ala Thr Ile Met Gly Met Ser Gln Phe Thr Thr Ala Ser His
            515                 520                 525
Ile Ala Arg Ala Ala Val Glu Gly Val Cys Phe Gln Ala Arg Ala Ile
530                 535                 540
Leu Lys Ala Met Ser Ser Asp Ala Phe Gly Glu Gly Ser Lys Asp Arg
545                 550                 555                 560
Asp Phe Leu Glu Glu Ile Ser Asp Val Thr Tyr Glu Lys Ser Pro Leu
                    565                 570                 575
Ser Val Leu Ala Val Asp Gly Gly Met Ser Arg Ser Asn Glu Val Met
                580                 585                 590
Gln Ile Gln Ala Asp Ile Leu Gly Pro Cys Val Lys Val Arg Arg Ser
            595                 600                 605
Pro Thr Ala Glu Cys Thr Ala Leu Gly Ala Ala Ile Ala Ala Asn Met
            610                 615                 620
Ala Phe Lys Asp Val Asn Glu Arg Pro Leu Trp Lys Asp Leu His Asp
625                 630                 635                 640
Val Lys Lys Trp Val Phe Tyr Asn Gly Met Glu Lys Asn Glu Gln Ile
                    645                 650                 655
Ser Pro Glu Ala His Pro Asn Leu Lys Ile Phe Arg Ser Glu Ser Asp
                660                 665                 670
Asp Ala Glu Arg Arg Lys His Trp Lys Tyr Trp Glu Val Ala Val Glu
            675                 680                 685
Arg Ser Lys Gly Trp Leu Lys Asp Ile Glu Gly Glu His Glu Gln Val
690                 695                 700
Leu Glu Asn Phe Gln
705

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GCGCGGATCC AGGAGTCTAG AATTATGGGA TTGACTACTA AACCTCTATC T          51

(2) INFORMATION FOR SEQ ID NO: 17:
```

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 17:

GATACGCCCG GGTTACCATT TCAACAGATC GTCCTT                36

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TTGATAATAT AACCATGGCT GCTGCTGCTG ATAG                  34

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GTATGATATG TTATCTTGGA TCCAATAAAT CTAATCTTC             39

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CATGACTAGT AAGGAGGACA ATTC                             24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CATGGAATTG TCCTCCTTAC TAGT                             24

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO: 22:

CTAGTAAGGA GGACAATTC                                                   19

(2) INFORMATION FOR SEQ ID NO: 23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 23:

CATGGAATTG TCCTCCTTA                                                   19

(2) INFORMATION FOR SEQ ID NO: 24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (xi) SEQUENCE DESCRIPTION: SEQ ID NO: 24:

GATCCAGGAA ACAGA                                                       15

(2) INFORMATION FOR SEQ ID NO: 25:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (xi) SEQUENCE DESCRIPTION: SEQ ID NO: 25:

CTAGTCTGTT TCCTG                                                       15

(2) INFORMATION FOR SEQ ID NO: 26:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 26:

GCTTTCTGTG CTGCGGCTTT AG                                               22
```

(2) INFORMATION FOR SEQ ID NO: 27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 27:

TGGTCGAGGA TCCACTTCAC TTT                                              23

(2) INFORMATION FOR SEQ ID NO: 28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 28:

AAAGTGAAGT GGATCCTCGA CCAATTGGAT GGTGGCGCAG TAGCAAACAA T               51

(2) INFORMATION FOR SEQ ID NO: 29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 29:

GGATCACCGC CGCAGAAACT ACG                                              23

(2) INFORMATION FOR SEQ ID NO: 30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 30:

CTGTCAGCCG TTAAGTGTTC CTGTG                                            25

(2) INFORMATION FOR SEQ ID NO: 31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 31:

CAGTTCAACC TGTTGATAGT ACG                                              23

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 32:

ATGAGTCAAA CATCAACCTT                                                      20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 33:

ATGGAGAAAA AAATCACTGG                                                      20

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 34:

TTACGCCCCG CCCTGCCACT                                                      20

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 35:

TCAGAGGATG TGCACCTGCA                                                      20

(2) INFORMATION FOR SEQ ID NO: 36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 36:

CGAGCATGCC GCATTTGGCA CTACTC                                    26

(2) INFORMATION FOR SEQ ID NO: 37:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(xi) SEQUENCE DESCRIPTION: SEQ ID NO: 37:

GCGTCTAGAG TAGGTTATTC CCACTCTTG                                 29

(2) INFORMATION FOR SEQ ID NO: 38:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(xi) SEQUENCE DESCRIPTION: SEQ ID NO: 38:

GAAGTCGACC GCTGCGCCTT ATCCGG                                    26

(2) INFORMATION FOR SEQ ID NO: 39:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(xi) SEQUENCE DESCRIPTION: SEQ ID NO: 39:

CGCGTCGACG TTTACAATTT CAGGTGGC                                  28

(2) INFORMATION FOR SEQ ID NO: 40:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(xi) SEQUENCE DESCRIPTION: SEQ ID NO: 40:

GCAGCATGCT GGACTGGTAG TAG                                       23

(2) INFORMATION FOR SEQ ID NO: 41:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(xi) SEQUENCE DESCRIPTION: SEQ ID NO: 41:

-continued

```
CAGTCTAGAG TTATTGGCAA ACCTACC                                    27

(2) INFORMATION FOR SEQ ID NO: 42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 42:

GATGCATGCC CAGGGCGGAG ACGGC                                      25

(2) INFORMATION FOR SEQ ID NO: 43:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 43:

CTAACGATTG TTCTCTAGAG AAAATGTCC                                  29
```

The invention claimed is:

1. An isolated nucleic acid molecule consisting essentially of a variant SULT1C1 nucleic acid sequence, wherein said variant SULT1C1 nucleic acid sequence is selected from the group consisting of:
    (a) at least ten contiguous nucleotides of SEQ ID NO: 26, wherein said sequence includes nucleotide position 179 of SEQ ID NO: 26, with the proviso that the nucleotide at position 179 is cytosine; or
    (b) at least ten contiguous nucleotides of SEQ ID NO: 26, wherein said sequence includes nucleotide position 218 of SEQ ID NO: 26, with the proviso that the nucleotide at position 218 is adenine; or
    (c) at least ten contiguous nucleotides of SEQ ID NO: 26, wherein said sequence includes nucleotide position 332 of SEQ ID NO: 26, with the proviso that the nucleotide at position 332 is thymine; or
    (d) at least ten contiguous nucleotides of SEQ ID NO; 26, wherein said sequence includes nucleotide position 763 of SEQ ID NO: 26, with the proviso that the nucleotide at position 763 is guanine; or
    (e) the complement of (a), (b), (c), or (d).

2. The isolated nucleic acid molecule of claim 1, wherein the isolated nucleic acid molecule is from 10 to 100 nucleotides in length.

3. The isolated nucleic acid molecule of claim 1, wherein the isolated nucleic acid molecule is from 20 to 50 nucleotides in length.

4. A vector comprising the nucleic acid molecule of claim 1.

5. The vector of claim 4, wherein the nucleic acid molecule is from 20 to 50 nucleotides in length.

* * * * *

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

Columns 23-70, Sequence Listing, please delete the entire Sequence Listing and replace with the following

-- SEQUENCE LISTING

<110> Freimuth, Robert R.
Weinshilboum, Richard M
Wieben, Eric D.

<120> SULFOTRANSFERASE SEQUENCE VARIANTS

<130> 07039-273001

<140> 09/792,695
<141> 2001-02-23

<160> 37

<170> FastSEQ for Windows Version 4.0

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

<210> 1
<211> 1380
<212> DNA
<213> Homo sapiens

<400> 1
```
tccagcctgg gcaacaggag tgaaacacca tctcaaaaaa aaaaaaaaaa aagaaaaaag    60
aaagaaaaag aaagttcaat ttattgggaa aaaaagagcc ctttggaaac aaggaggaag   120
aagaagtgtc ggcaaagaag cattaggagg ttcagggtca aagaagacaa ggaaagcttt   180
ggcaagaagg gcagatgggg tgcagaatta tgcttcaatt ccagaaagga aagcactggg   240
gtagatacaa ggttggggct ggcagaagag tagcagttca gagatcatta acacttgatc   300
catttaattt cccaggtaac caaagacacc atggaatata atctgcctcc actaaagtgt   360
acctttgta caataaggca aagaaaaaat aagtacacac ctaagctcta gacttttgtt   420
ctatcctctc tgcattttcg gtgtggatga atacaacttg ggaagaaagg aaagaagaac   480
cagcagtttt aagcacttac tatttgctct gcaaagtgta ttcatcaaca ttgttgcttt   540
caatcttaaa gcatggattg gagacaggca gtattaccca cacttcatag atgcagaaat   600
taaatctcag gctaaggagg aaggaaaagg gagttcacca aataagcagg agcctacctg   660
aagcctgatg catctggtcc tagagccaac cttccatttc cccccagccc ccacctgttt   720
aagcttcgag gccagtggga ggagggaggg gccaggcagc tgagggccag gaaagatgtg   780
aaaaactcta gctggtgacc gagaggagga gtagagtgtg cccttagttc atatgaacta   840
gagggagttg gtatttgcac agcagtcagg gtcacatgag tgatcatggt acagtgagaa   900
```

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

```
gttctccctc ccagggccag gtcacagggt ttgtttctgt tcaatccgga ttcttccagt    960
aaaagcttca acttcccaca ctgaagctga gagcctccca aagtgctggc tacctgctga   1020
gcgccccgt aactctgaca cagtagtaat ttgagcctct gcaattgccg tctgcttcct   1080
gtgaaagtcc tttccgtgcc cactgaccct tgagtgggcc tttgagctgc tgactttcag   1140
ctggaacttg aaggtaagaa tatggcttaa aagaaattct gtacctaact cgttaattta   1200
ttttttaacc tttagccaca taggtgtggc tttacagatg catttattca aaccagaaaa   1260
gatcctaaga atctgataaa ataatataaa agagttttgt taacagcctc cagcctaaaa   1320
attcagacct agaaattcag gaccccctc aaatcacctc caaaagctct ctctcctgta   1380
```

<210> 2
<211> 296
<212> PRT
<213> Homo sapiens

<400> 2
Met Ala Leu Thr Ser Asp Leu Gly Lys Gln Ile Lys Leu Lys Glu Val
 1               5                  10                  15
Glu Gly Thr Leu Leu Gln Pro Ala Thr Val Asp Asn Trp Ser Gln Ile
            20                  25                  30
Gln Ser Phe Glu Ala Lys Pro Asp Asp Leu Leu Ile Cys Thr Tyr Pro
        35                  40                  45

UNITED STATES PATENT AND TRADEMARK OFFICE
CERTIFICATE OF CORRECTION

PATENT NO.       : 7,026,163 B1
APPLICATION NO.  : 09/792695
DATED            : April 11, 2006
INVENTOR(S)      : Freimuth et al.

It is certified that error appears in the above-identified patent and that said Letters Patent is hereby corrected as shown below:

```
Lys Ala Gly Thr Thr Trp Ile Gln Glu Ile Val Asp Met Ile Glu Gln
    50              55              60
Asn Gly Asp Val Glu Lys Cys Gln Arg Ala Ile Ile Gln His Arg His
65              70              75              80
Pro Phe Ile Glu Trp Ala Arg Pro Pro Gln Pro Ser Gly Val Glu Lys
            85              90              95
Ala Lys Ala Met Pro Ser Pro Arg Ile Leu Lys Thr His Leu Ser Thr
            100             105             110
Gln Leu Leu Pro Pro Ser Phe Trp Glu Asn Asn Cys Lys Phe Leu Tyr
        115             120             125
Val Ala Arg Asn Ala Lys Asp Cys Met Val Ser Tyr Tyr His Phe Gln
    130             135             140
Arg Met Asn His Met Leu Pro Asp Pro Gly Thr Trp Glu Glu Tyr Phe
145             150             155             160
Glu Thr Phe Ile Asn Gly Lys Val Val Trp Gly Ser Trp Phe Asp His
            165             170             175
Val Lys Gly Trp Trp Glu Met Lys Asp Arg His Gln Ile Leu Phe Leu
            180             185             190
Phe Tyr Glu Asp Ile Lys Arg Asp Pro Lys His Glu Ile Arg Lys Val
        195             200             205
```

UNITED STATES PATENT AND TRADEMARK OFFICE
CERTIFICATE OF CORRECTION

PATENT NO.       : 7,026,163 B1
APPLICATION NO.  : 09/792695
DATED            : April 11, 2006
INVENTOR(S)      : Freimuth et al.

It is certified that error appears in the above-identified patent and that said Letters Patent is hereby corrected as shown below:

```
Met Gln Phe Met Gly Lys Lys Val Asp Glu Thr Val Leu Asp Lys Ile
   210             215              220
Val Gln Glu Thr Ser Phe Glu Lys Met Lys Glu Asn Pro Met Thr Asn
225             230             235             240
Arg Ser Thr Val Ser Lys Ser Ile Leu Asp Gln Ser Ile Ser Ser Phe
        245             250             255
Met Arg Lys Gly Thr Val Gly Asp Trp Lys Asn His Phe Thr Val Ala
           260             265             270
Gln Asn Glu Arg Phe Asp Glu Ile Tyr Arg Arg Lys Met Glu Gly Thr
       275             280             285
Ser Ile Asn Phe Cys Met Glu Leu
   290             295
```

<210> 3
<211> 30
<212> DNA
<213> Homo sapiens

<400> 3
tctctccttc ctcttttctc tctccctccc        30

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 4
<211> 56
<212> DNA
<213> Artificial Sequence

<220>
<223> primer for PCR

<400> 4
tgtaaaacga cggccagtgt acaataaggc aaagaaaaaa taagtacaca cctaag      56

<210> 5
<211> 42
<212> DNA
<213> Artificial Sequence

<220>
<223> primer for PCR

<400> 5
caggaaacag ctatgaccca ctctactcct cctctcggtc ac      42

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 6
<211> 48
<212> DNA
<213> Artificial Sequence

<220>
<223> primer for PCR

<400> 6
tgtaaaacga cggccagtgg aaagatgtga aaaactctag ctggtgac          48

<210> 7
<211> 53
<212> DNA
<213> Artificial Sequence

<220>
<223> primer for PCR

<400> 7
caggaaacag ctatgacctt tgaataaatg catctgtaaa gccacaccta tgt          53

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 8
<211> 53
<212> DNA
<213> Artificial Sequence

<220>
<223> primer for PCR

<400> 8
tgtaaaacga cggccagtaa tgtgaatgta cttaatgcct ctgaactgta cac      53

<210> 9
<211> 49
<212> DNA
<213> Artificial Sequence

<220>
<223> primer for PCR

<400> 9
caggaaacag ctatgaccca ttgtggaaca ataagaagga gcaggtttc      49

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

<210> 10
<211> 45
<212> DNA
<213> Artificial Sequence

<220>
<223> primer for PCR

<400> 10
tgtaaaacga cggccagtat ggcaaacagg attctgaccc aaggg           45

<210> 11
<211> 53
<212> DNA
<213> Artificial Sequence

<220>
<223> primer for PCR

<400> 11
caggaaacag ctatgaccga aacatatgac agtgaaaatg agagagaaag aga           53

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 12
<211> 49
<212> DNA
<213> Artificial Sequence

<220>
<223> primer for PCR

<400> 12
tgtaaaacga cggccagtgc acttttttt gagacagggt ctcactctg         49

<210> 13
<211> 49
<212> DNA
<213> Artificial Sequence

<220>
<223> primer for PCR

<400> 13
caggaaacag ctatgaccgg gaaaagccct atgaacaaga gctagaaaa         49

UNITED STATES PATENT AND TRADEMARK OFFICE
CERTIFICATE OF CORRECTION

PATENT NO.         : 7,026,163 B1
APPLICATION NO. : 09/792695
DATED                : April 11, 2006
INVENTOR(S)       : Freimuth et al.

It is certified that error appears in the above-identified patent and that said Letters Patent is hereby corrected as shown below:

<210> 14
<211> 57
<212> DNA
<213> Artificial Sequence

<220>
<223> primer for PCR

<400> 14
tgtaaaacga cggccagtat taataatccc attgtaaaat cccaaaagaa agtcaag      57

<210> 15
<211> 55
<212> DNA
<213> Artificial Sequence

<220>
<223> primer for PCR

<400> 15
caggaaacag ctatgaccgc tgaatgtaga actttatgtt ttctctttgc tggta      55

UNITED STATES PATENT AND TRADEMARK OFFICE
CERTIFICATE OF CORRECTION

PATENT NO.        : 7,026,163 B1
APPLICATION NO. : 09/792695
DATED             : April 11, 2006
INVENTOR(S)       : Freimuth et al.

It is certified that error appears in the above-identified patent and that said Letters Patent is hereby corrected as shown below:

<210> 16
<211> 41
<212> DNA
<213> Artificial Sequence

<220>
<223> primer for PCR

<400> 16
tgtaaaacga cggccagtag ggccagcact gcagaactga g            41

<210> 17
<211> 42
<212> DNA
<213> Artificial Sequence

<220>
<223> primer for PCR

<400> 17
caggaaacag ctatgaccac actcagtggc cagcttgctc tg           42

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 18
<211> 48
<212> DNA
<213> Artificial Sequence

<220>
<223> primer for PCR

<400> 18
tgtaaaacga cggccagtct acaccaccct caaaatcaaa cagatcag        48

<210> 19
<211> 45
<212> DNA
<213> Artificial Sequence

<220>
<223> primer for PCR

<400> 19
caggaaacag ctatgaccgc ggcaagggta acattggact ggaat        45

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 20
<211> 56
<212> DNA
<213> Artificial Sequence

<220>
<223> primer for PCR

<400> 20
tgtaaaacga cggccagttg tagtatttct ttatgatact ctcattcatt ccagtc         56

<210> 21
<211> 51
<212> DNA
<213> Artificial Sequence

<220>
<223> primer for PCR

<400> 21
caggaaacag ctatgaccct agaaagctct cttctacaac aggatcaaat c         51

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 22
<211> 46
<212> DNA
<213> Artificial Sequence

<220>
<223> primer for PCR

<400> 22
tgtaaaacga cggccagtac cgagtcccct aggcctgctt cttata            46

<210> 23
<211> 55
<212> DNA
<213> Artificial Sequence

<220>
<223> primer for PCR

<400> 23
caggaaacag ctatgaccgt actacattgt atacattcac aatatgcttt cagag            55

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 24
<211> 46
<212> DNA
<213> Artificial Sequence

<220>
<223> primer for PCR

<400> 24
tgtaaaacga cggccagtac tatcttcaat ccttcagtcc cagcca        46

<210> 25
<211> 42
<212> DNA
<213> Artificial Sequence

<220>
<223> primer for PCR

<400> 25
caggaaacag ctatgaccga gttcggtgaa tggccaggac ag        42

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<210> 26
<211> 891
<212> DNA
<213> Homo sapiens

<220>
<221> CDS
<222> (1)...(888)

<400> 26
```
atg gcc ctg acc tca gac ctg ggg aaa cag ata aaa ctg aaa gag gtg    48
Met Ala Leu Thr Ser Asp Leu Gly Lys Gln Ile Lys Leu Lys Glu Val
 1               5                  10                  15 gag ggg acc ctc ctg cag cct gca act gtg gac aac tgg agc cag atc    96
Glu Gly Thr Leu Leu Gln Pro Ala Thr Val Asp Asn Trp Ser Gln Ile
            20                  25                  30 cag agc ttc gag gcc aaa cca gat gat ctc ctc atc tgc acc tac cct   144
Gln Ser Phe Glu Ala Lys Pro Asp Asp Leu Leu Ile Cys Thr Tyr Pro
        35                  40                  45
```

UNITED STATES PATENT AND TRADEMARK OFFICE
CERTIFICATE OF CORRECTION

PATENT NO.       : 7,026,163 B1
APPLICATION NO.  : 09/792695
DATED            : April 11, 2006
INVENTOR(S)      : Freimuth et al.

It is certified that error appears in the above-identified patent and that said Letters Patent is hereby corrected as shown below:

aaa gca ggg aca acg tgg att cag gaa att gtg gat atg att gaa cag     192
Lys Ala Gly Thr Thr Trp Ile Gln Glu Ile Val Asp Met Ile Glu Gln
    50              55              60 aat ggg gac gtg gag aag tgc cag cga gcc atc atc caa cac cgc cat     240
Asn Gly Asp Val Glu Lys Cys Gln Arg Ala Ile Ile Gln His Arg His
    65              70              75              80 cct ttc att gag tgg gct cgg cca ccc caa cct tct ggt gtg gaa aaa     288
Pro Phe Ile Glu Trp Ala Arg Pro Pro Gln Pro Ser Gly Val Glu Lys
        85              90              95 gcc aaa gca atg ccc tct cca cgg ata cta aag act cac ctt tcc act     336
Ala Lys Ala Met Pro Ser Pro Arg Ile Leu Lys Thr His Leu Ser Thr
        100             105             110 cag ctg ctg cca ccg tct ttc tgg gaa aac aac tgc aag ttc ctt tat     384
Gln Leu Leu Pro Pro Ser Phe Trp Glu Asn Asn Cys Lys Phe Leu Tyr
        115             120             125

UNITED STATES PATENT AND TRADEMARK OFFICE
CERTIFICATE OF CORRECTION

PATENT NO.        : 7,026,163 B1
APPLICATION NO.   : 09/792695
DATED             : April 11, 2006
INVENTOR(S)       : Freimuth et al.

It is certified that error appears in the above-identified patent and that said Letters Patent is hereby corrected as shown below:

```
gta gct cga aat gcc aaa gac tgt atg gtt tcc tac tac cat ttc caa    432
Val Ala Arg Asn Ala Lys Asp Cys Met Val Ser Tyr Tyr His Phe Gln
    130             135             140 agg atg aac cac atg ctt cct gac cct ggt acc tgg gaa gag tat ttt    480
Arg Met Asn His Met Leu Pro Asp Pro Gly Thr Trp Glu Glu Tyr Phe
145             150             155             160 gaa acc ttc atc aat gga aaa gtg gtt tgg ggt tcc tgg ttt gac cac    528
Glu Thr Phe Ile Asn Gly Lys Val Val Trp Gly Ser Trp Phe Asp His
        165             170             175 gtg aaa gga tgg tgg gag atg aaa gac aga cac cag att ctc ttc ctc    576
Val Lys Gly Trp Trp Glu Met Lys Asp Arg His Gln Ile Leu Phe Leu
        180             185             190 ttc tat gag gac ata aag agg gac cca aag cat gaa att cgg aag gtg    624
Phe Tyr Glu Asp Ile Lys Arg Asp Pro Lys His Glu Ile Arg Lys Val
            195             200             205
```

UNITED STATES PATENT AND TRADEMARK OFFICE
CERTIFICATE OF CORRECTION

| | | |
|---|---|---|
| PATENT NO. | : 7,026,163 B1 | |
| APPLICATION NO. | : 09/792695 | |
| DATED | : April 11, 2006 | |
| INVENTOR(S) | : Freimuth et al. | |

It is certified that error appears in the above-identified patent and that said Letters Patent is hereby corrected as shown below:

```
atg cag ttc atg gga aag aag gtg gat gaa aca gtg cta gat aaa att    672
Met Gln Phe Met Gly Lys Lys Val Asp Glu Thr Val Leu Asp Lys Ile
    210             215             220 gtc cag gag acg tca ttt gag aaa atg aaa gaa aat ccc atg aca aat    720
Val Gln Glu Thr Ser Phe Glu Lys Met Lys Glu Asn Pro Met Thr Asn
225             230             235             240 cgt tct aca gtt tcc aaa tct atc ttg gac cag tca att tcc tcc ttc    768
Arg Ser Thr Val Ser Lys Ser Ile Leu Asp Gln Ser Ile Ser Ser Phe
        245             250             255 atg aga aaa gga act gtg ggg gat tgg aaa aac cac ttc act gtt gcc    816
Met Arg Lys Gly Thr Val Gly Asp Trp Lys Asn His Phe Thr Val Ala
        260             265             270 cag aat gag agg ttt gat gaa atc tat aga aga aag atg gaa gga acc    864
Gln Asn Glu Arg Phe Asp Glu Ile Tyr Arg Arg Lys Met Glu Gly Thr
        275             280             285
```

UNITED STATES PATENT AND TRADEMARK OFFICE
CERTIFICATE OF CORRECTION

| | | |
|---|---|---|
| PATENT NO. | : 7,026,163 B1 | Page 21 of 33 |
| APPLICATION NO. | : 09/792695 | |
| DATED | : April 11, 2006 | |
| INVENTOR(S) | : Freimuth et al. | |

It is certified that error appears in the above-identified patent and that said Letters Patent is hereby corrected as shown below:

```
cc ata aac ttc tgc atg gaa ctc tga                 891
   Ser Ile Asn Phe Cys Met Glu Leu
      290             295
```

<210> 27
<211> 1087
<212> DNA
<213> Homo sapiens

<400> 27

```
tttcccatag ggacccccaac cctgagacac tatggccctg acctcagacc tggggaaaca     60
gataaaactg aaagaggtgg aggggaccct cctgcagcct gcaactgtgg acaactggag    120
ccagatccag agcttcgagg ccaaaccaga tgatctcctc atctgcacct accctaaagc    180
aggtgattgc agggtaggag ggacagcaaa gacctgctga gccagcacag gctcatcact    240
taagttagaa ttcccttct taggaaacct gctccttctt attgttccac aatgggtttt    300
ggagctcagg gctcacacag gatgcctgat atccgagttt tccaggaaag ctgctatgct    360
ctaccatgca ctggtcttgg gtggagagac ccttgcctgt gctgctccac tccctacaga    420
gatccaaagt ccatccctca tggacttcta tcactcatgg caaacaggat tctgacccaa    480
ggggaggggtg atgcaaacac caaggctcta catcctcttc gtttactcgg gactcttcag    540
ggaagattgt ctaacagatt tctgcttctc atccttcctt tctgagcctc agggacaacg    600
tggattcagg aaattgtgga tatgattgaa cagaatgggg acgtggagaa gtgccagcga    660
```

UNITED STATES PATENT AND TRADEMARK OFFICE
CERTIFICATE OF CORRECTION

| | | |
|---|---|---|
| PATENT NO. | : 7,026,163 B1 | Page 22 of 33 |
| APPLICATION NO. | : 09/792695 | |
| DATED | : April 11, 2006 | |
| INVENTOR(S) | : Freimuth et al. | |

It is certified that error appears in the above-identified patent and that said Letters Patent is hereby corrected as shown below:

```
gccatcatcc aacaccgcca tcctttcatt gagtgggctc ggccacccca accttctggt    720
gagagcacct ccctctttct ctcttcctgc tttctttccc tctctcttct gttttcccct    780
gtcttttctc acttttctcc tcttctctcc tctctctctc ccccatctct ccttcctctt    840
ttctctctcc ctcccctctct ccttcctctt ctctttctct ctcattttca ctgtcatatg    900
tttcttcctt ttatcttcct ctcatcctct gtctacatat tatttaagat tttttaccaa    960
aagtgaatca ccaaatgaaa aggatgtgtg ctagggtcag attctgcctt attttcttct   1020
taagccctcc ctctgatcat gtgcaactgt agatcacatt gaagatgtga aaaactgtaa   1080
gccattt                                                            1087
```

<210> 28
<211> 667
<212> DNA
<213> Homo sapiens

<400> 28
```
tgttttcaac ttctcttttt attcctttgc acttttttttt gagacagggt ctcactctgt     60
cacccaggct agagtgcagt agtgcaaaca cagctcactg cagcctcaat tctctcgagc    120
tcaagcgatc ctcccatctc agcctcccga gtaagtagct gggactacag gtgcgtatca    180
ccatgcccag ctaattttgg tatttttttt tttagagac aggatttcac catgttgccc    240
aggctggtct caaactcctg agctcaagca atccacctgc ctcaacctcc caaagtgcca    300
agattacaga cgtgagccac tgcccctggc cttctttgca tattttaaac atagttattt    360
```

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

```
atattctcta ttaggtaccc aataactgag gtcactaggg gtttagttct tccacctgtt    420
tttttctag ctcttgttca tagggctttt ccctcatttg ttttgtaatt ttgtataaaa    480
agctctttc tccctgtctt gatctcacac ctacattgga acatttccaa tctagaatag    540
tttaagttaa cttctggtcc aagctggtag tataatttca tatccatgca tgtagtatga    600
aaacaggatt gtggttatga gttctcaaga aagcctcttt ttctgcaccc agaggcgagg    660
caaggaa                                                              667

<210> 29
<211> 799
<212> DNA
<213> Homo sapiens

<400> 29
tgctgcaggc acatgggggt catctctggc tggcaggaag gtgagggagt cctctcttct    60
ctggtcctgg ctgactctgc ctcagcagga cttcacttga ccattctcac cttctgtcac   120
ctcatcctta aagtgacaga gtaaattaac tctaaggccc catccaggac tcaagctgtg   180
tgattttaca aaaatgaaaa ttatattaat aatcccattg taaaatccca aaagaaagtc   240
aagagactag cagaaagaca ggtgggtgat gggatgtcct ggacagagcc tggatcatga   300
ggtccccatg tagtgcttgt actacgcaga tgtttcctct tgagctattt taaaggtgtg   360
gaaaagcca aagcaatgcc ctctccacgg atactaaaga ctcacctttc cactcagctg   420
ctgccaccgt ctttctggga aaacaactgc aaggtaagat accaacagct ccctgtgaca   480
```

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

```
gaagggaaag taagccaacc aaagcgagtc ctgcagaccc caacgcagag cattcgtgat    540
caccttttgcc tctccactgt ctctgatgct taccagcaaa gagaaaacat aaagttctac   600
attcagcagg acattcacct gaacagtttc aaataggaca tgaaggcagg atccagattg    660
aatgtttgga gggaactaga gacatgggga ggcagtgagt gcagtaagcg tagctgtgaa    720
atgaagggga gaagatggtg gtcccaggct gcaggccatg gggaggtttt ctaacagacc    780
agggagggaa gaatgagag                                                 799

<210> 30
<211> 1304
<212> DNA
<213> Homo sapiens

<400> 30
aagtccactt tttataccat cttttaccca cctcttttct taccccaaag ttcctttatg    60
tagctcgaaa tgccaaagac tgtatggttt cctactacca tttccaaagg atgaaccaca    120
tgcttcctga ccctggtacc tgggaagagt attttgaaac cttcatcaat ggaaaaggta    180
cgggaacatc cttcacaccc ttgcattctc actccagcta ggctgggtct agggaaccac    240
aggcagcatt ttatccccta gaatgcctgt acttcatcag gtgtgtccta ccacagactg    300
ggactgggca gagcaagctg gccactgagt gtatgcccac agccctcagc aaacatcttc    360
cacctgattc agagtcttta attacagcca tcctcttcca aaaggtgtcc ttgtccctat    420
gtgattgcac ataataggaa gccactttag ggacgatgtt ggggcaagta accctaaggc    480
```

UNITED STATES PATENT AND TRADEMARK OFFICE
CERTIFICATE OF CORRECTION

| | | |
|---|---|---|
| PATENT NO. | : 7,026,163 B1 | |
| APPLICATION NO. | : 09/792695 | |
| DATED | : April 11, 2006 | |
| INVENTOR(S) | : Freimuth et al. | |

It is certified that error appears in the above-identified patent and that said Letters Patent is hereby corrected as shown below:

```
tgtccccatc tacaccaccc tcaaaatcaa acagatcaga acccttagga catatctaat     540
acagaatttg ggttttctct ctctaactca cttcaggaaa atccctaata ctcagaaggt    600
tttgtgtgat gcctatgtag actattctgt ttcctgtgtc tatttcagtg gtttggggtt    660
cctggtttga ccacgtgaaa ggatggtggg agatgaaaga cagacaccag attctcttcc   720
tcttctatga ggacataaag agggtgagtg aaggctctgc agaagaacca ttttaaagtg    780
gttcttcagg tgcagagaaa ttcaaagttg tttcaaagga catcccagag aattgtagta   840
tttctttatg atactctcat tcattccagt ccaatgttac ccttgccgca ggacccaaag   900
catgaaattc ggaaggtgat gcagttcatg ggaaagaagg tggatgaaac agtgctagat   960
aaaattgtcc aggagacgtc atttgagaaa atgaaagaaa atcccatgac aaatcgttct   1020
acagtttcca aatctatctt ggaccagtca atttcctcct tcatgagaaa aggtgtgtgg   1080
ggcctcttta tcatacattc agattgtctc gtaacatcct gtctgcctct tagcagacaa   1140
tattgagttt tattaattcc aagccaatgc atttcaacta ttcctaatat gtgtttctaa   1200
taaaaccagg gatttgatcc tgttgtagaa gagagctttc tagggtattg ttccagtatt   1260
tggttgcaag gaacagagag tccctcaagc tagccccaaa gaaa                      1304
```

<210> 31
<211> 1080
<212> DNA
<213> Homo sapiens

<400> 31

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

```
ttgctcaaca taatgttttg agattcctcc atgtggttgt gtgtctgtag ttcatcattc    60
ttttatgtct atgtagtaat ccatcaggta aatacactac aggtggggcc aggtcatgca   120
ggccactagc tgccttgggt cagttgtcca gctgacttag aagtccatcc ccctgcacag   180
agtcccctag gcctgcttct tataggagag ctgctcatgg acaggtgtcc actgaagggg   240
gagttgggtg agtcaggtat gtggacaggc cagattcagt atgggcacta caccacttta   300
ctcagggaca ccacatcttt caatcagagt gacactcctg tctggccttc cttttctag    360
gaactgtggg ggattggaaa aaccacttca ctgttgccca gaatgagagg tttgatgaaa   420
tctatagaag aaagatggaa ggaacctcca taaacttctg catggaactc tgagcaagat   480
gtaaataaaa ttaaaaggtg gatggcaaga gtgcaaatac tatcttcaat ccttcagtcc   540
cagccagaag aatctctgaa agcatattgt gaatgtatac aatgtagtac aaacaatctc   600
tgtgatgatt aacagtatgt caccacttca tttttaaaa aggatcacgt ctaatgccca    660
ttttcccaac tattcttcc aaagtaagat ataaggtagc ttaataaact aagtaaaacg    720
tatgacttga gtacaaaagg attgttttaa tccccattat tctggaaagt gcatcctagt   780
ctcccagtct ataacatcat aataccttga gtataagtcc aaatattagg ttatatctat   840
attaaaaaca aaatttctgt catctgtcct ggccattcag gcaactccag cctgggctca   900
atcctggagt tctgtctggt cactatcaga aggaacactt tgagggaaac cctggtgcag   960
ccagccctga ggaaacatgg cctgagtgcc ctcactggtg ggtgggaata aaatggaagt  1020
gcacagagga gatgtcagaa gaccaaaact tggtgaatag tcccagtgct aggtcatata  1080
```

<210> 32
<211> 1380

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

<212> DNA
<213> Homo sapiens

<400> 32
tacaggagag agagcttttg gaggtgattt gagggggtc ctgaatttct aggtctgaat    60
ttttaggctg gaggctgtta acaaaactct tttatattat tttatcagat tcttaggatc   120
ttttctggtt tgaataaatg catctgtaaa gccacaccta tgtggctaaa ggttaaaaaa   180
taaattaacg agttaggtac agaatttctt ttaagccata ttcttaccct caagttccag   240
ctgaaagtca gcagctcaaa ggcccactca agggtcagtg ggcacggaaa ggactttcac   300
aggaagcaga cggcaattgc agaggctcaa attactactg tgtcagagtt acggggcgc    360
tcagcaggta gccagcactt tgggaggctc tcagcttcag tgtgggaagt tgaagctttt   420
actggaagaa tccggattga acagaaacaa accctgtgac ctggccctgg gagggagaac   480
ttctcactgt accatgatca ctcatgtgac cctgactgct gtgcaaatac caactccctc   540
tagttcatat gaactaaggg cacactctac tcctcctctc ggtcaccagc tagagttttt   600
cacatctttc ctggccctca gctgcctggc ccctccctcc tcccactggc ctcgaagctt   660
aaacaggtgg gggctggggg gaaatggaag gttggctcta ggaccagatg catcaggctt   720
caggtaggct cctgcttatt tggtgaactc ccttttcctt cctccttagc ctgagattta   780
atttctgcat ctatgaagtg tgggtaatac tgcctgtctc caatccatgc tttaagattg   840
aaagcaacaa tgttgatgaa tacactttgc agagcaaata gtaagtgctt aaaactgctg   900
gttcttcttt cctttcttcc caagttgtat tcatccacac cgaaaatgca gagaggatag   960
aacaaaagtc tagagcttag gtgtgtactt attttttctt tgccttattg tacaaaaggt  1020

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

```
acactttagt ggaggcagat tatattccat ggtgtctttg gttacctggg aaattaaatg   1080
gatcaagtgt taatgatctc tgaactgcta ctcttctgcc agccccaacc ttgtatctac   1140
cccagtgctt tcctttctgg aattgaagca taattctgca ccccatctgc ccttcttgcc   1200
aaagctttcc ttgtcttctt tgaccctgaa cctcctaatg cttctttgcc gacacttctt   1260
cttcctcctt gtttccaaag ggctcttttt ttcccaataa attgaactt cttttttcttt   1320
cttttttctt tttttttttt tttttgaga tggtgtttca ctcctgttgc ccaggctgga   1380

<210> 33
<211> 1086
<212> DNA
<213> Homo sapiens

<400> 33
aaatggctta cagttttca catcttcaat gtgatctaca gttgcacatg atcagaggga    60
gggcttaaga agaaaataag gcagaatctg accctagcac acatccttt catttggtga   120
ttcacttttg gtaaaaaatc ttaaataata tgtagacaga ggatgagagg aagataaaag   180
gaagaaacat atgacagtga aaatgagaga gaaagagaag aggaaggaga gagggaggga   240
gagagaaaag aggaaggaga gatgggggag agagagagga gagaagagga gaaaagtgag   300
aaaagacagg ggaaaacaga agagagaggg aaagaaagca ggaagagaga aagagggagg   360
tgctctcacc agaaggttgg ggtggccgag cccactcaat gaaaggatgg cggtgttgga   420
tgatggctcg ctggcacttc tccacgtccc cattctgttc aatcatatcc acaatttcct   480
```

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

```
gaatccacgt tgtccctgag gctcagaaag gaaggatgag aagcagaaat ctgttagaca    540
atcttccctg aagagtcccg agtaaacgaa gaggatgtag agccttggtg tttgcatcac    600
cctccccttg ggtcagaatc ctgtttgcca tgagtgatag aagtccatga gggatggact    660
ttggatctct gtagggagtg gagcagcaca ggcaagggtc tctccaccca agaccagtgc    720
atggtagagc atagcagctt tcctggaaaa ctcggatatc aggcatcctg tgtgagccct    780
gagctccaaa acccattgtg gaacaataag aaggagcagg tttcctaaga aggggaattc    840
taacttaagt gatgagcctg tgctggctca gcaggtcttt gctgtccctc ctaccctgca    900
atcacctgct ttagggtagg tgcagatgag gagatcatct ggtttggcct cgaagctctg    960
gatctggctc cagttgtcca cagttgcagg ctgcaggagg gtccctcca cctctttcag   1020
ttttatctgt ttccccaggt ctgaggtcag ggccatagtg tctcagggtt ggggtcccta   1080
tgggaa                                                             1086

<210> 34
<211> 667
<212> DNA
<213> Homo sapiens

<400> 34
ttccttgcct cgcctctggg tgcagaaaaa gaggctttct tgagaactca taaccacaat     60
cctgttttca tactacatgc atggatatga aattatacta ccagcttgga ccagaagtta    120
acttaaacta ttctagattg gaaatgttcc aatgtaggtg tgagatcaag acagggagaa    180
```

UNITED STATES PATENT AND TRADEMARK OFFICE
CERTIFICATE OF CORRECTION

PATENT NO.       : 7,026,163 B1
APPLICATION NO.  : 09/792695
DATED            : April 11, 2006
INVENTOR(S)      : Freimuth et al.

It is certified that error appears in the above-identified patent and that said Letters Patent is hereby corrected as shown below:

```
aagagctttt tatacaaaat tacaaaacaa atgagggaaa agccctatga acaagagcta    240
gaaaaaaaac aggtggaaga actaaacccc tagtgacctc agttattggg tacctaatag    300
agaatataaa taactatgtt taaaatatgc aaagaaggcc aggggcagtg gctcacgtct    360
gtaatcttgg cactttggga ggttgaggca ggtggattgc ttgagctcag gagtttgaga    420
ccagcctggg caacatggtg aaatcctgtc tctaaaaaaa aaaaatacca aaattagctg    480
ggcatggtga tacgcacctg tagtcccagc tacttactcg ggaggctgag atgggaggat    540
cgcttgagct cgagagaatt gaggctgcag tgagctgtgt ttgcactact gcactctagc    600
ctgggtgaca gagtgagacc ctgtctcaaa aaaagtgca aaggaataaa agagaaagtt    660
gaaaaca                                                 667

<210> 35
<211> 799
<212> DNA
<213> Homo sapiens

<400> 35
ctctcattct tccctccctg gtctgttaga aaacctcccc atggcctgca gcctgggacc    60
accatcttct cccttcatt tcacagctac gcttactgca ctcactgcct ccccatgtct   120
ctagttccct ccaaacattc aatctggatc ctgccttcat gtcctatttg aaactgttca   180
ggtgaatgtc ctgctgaatg tagaacttta tgttttctct ttgctggtaa gcatcagaga   240
cagtggagag gcaaaggtga tcacgaatgc tctgcgttgg ggtctgcagg actcgctttg   300
```

UNITED STATES PATENT AND TRADEMARK OFFICE
CERTIFICATE OF CORRECTION

| | | |
|---|---|---|
| PATENT NO. | : 7,026,163 B1 | Page 31 of 33 |
| APPLICATION NO. | : 09/792695 | |
| DATED | : April 11, 2006 | |
| INVENTOR(S) | : Freimuth et al. | |

It is certified that error appears in the above-identified patent and that said Letters Patent is hereby corrected as shown below:

```
gttggcttac tttcccttct gtcacaggga gctgttggta tcttaccttg cagttgtttt    360
cccagaaaga cggtggcagc agctgagtgg aaaggtgagt cttagtatc cgtggagagg    420
gcattgcttt ggcttttcc acacctttaa aatagctcaa gaggaaacat ctgcgtagta    480
caagcactac atggggacct catgatccag gctctgtcca ggacatccca tcacccacct    540
gtctttctgc tagtctcttg actttctttt gggattttac aatgggatta ttaatataat    600
tttcatttt gtaaaatcac acagcttgag tcctggatgg ggccttagag ttaatttact    660
ctgtcacttt aaggatgagg tgacagaagg tgagaatggt caagtgaagt cctgctgagg    720
cagagtcagc caggaccaga gaagagagga ctccctcacc ttcctgccag ccagagatga    780
cccccatgtg cctgcagca                                                 799

<210> 36
<211> 1304
<212> DNA
<213> Homo sapiens

<400> 36
tttctttggg gctagcttga gggactctct gttccttgca accaaatact ggaacaatac     60
cctagaaagc tctcttctac aacaggatca aatccctggt tttattagaa acacatatta    120
ggaatagttg aaatgcattg gcttggaatt aataaaactc aatattgtct gctaagaggc    180
agacaggatg ttacgagaca atctgaatgt atgataaaga ggccccacac accttttctc    240
atgaaggagg aaattgactg gtccaagata gatttggaaa ctgtagaacg atttgtcatg    300
```

UNITED STATES PATENT AND TRADEMARK OFFICE
CERTIFICATE OF CORRECTION

PATENT NO. : 7,026,163 B1
APPLICATION NO. : 09/792695
DATED : April 11, 2006
INVENTOR(S) : Freimuth et al.

It is certified that error appears in the above-identified patent and that said Letters Patent is hereby corrected as shown below:

```
ggattttctt tcattttctc aaatgacgtc tcctggacaa ttttatctag cactgtttca    360
tccaccttct ttcccatgaa ctgcatcacc ttccgaattt catgctttgg gtcctgcggc    420
aagggtaaca ttggactgga atgaatgaga gtatcataaa gaaatactac aattctctgg   480
gatgtccttt gaaacaactt tgaatttctc tgcacctgaa gaaccactt aaaatggttc    540
ttctgcagag ccttcactca ccctctttat gtcctcatag aagaggaaga gaatctggtg   600
tctgtctttc atctcccacc atcctttcac gtggtcaaac caggaacccc aaaccactga   660
aatagacaca ggaaacagaa tagtctacat aggcatcaca caaaaccttc tgagtattag   720
ggattttcct gaagtgagtt agagagagaa aacccaaatt ctgtattaga tatgtcctaa   780
gggttctgat ctgtttgatt ttgagggtgg tgtagatggg gacagcctta gggttacttg   840
ccccaacatc gtccctaaag tggcttccta ttatgtcaa tcacataggg acaaggacac    900
cttttggaag aggatggctg taattaaaga ctctgaatca ggtggaagat gtttgctgag   960
ggctgtgggc atacactcag tggccagctt gctctgccca gtcccagtct gtggtaggac  1020
acacctgatg aagtacaggc attctagggg ataaaatgct gcctgtggtt ccctagaccc  1080
agcctagctg gagtgagaat gcaagggtgt gaaggatgtt cccgtacctt ttccattgat   1140
gaaggtttca aaatactctt cccaggtacc agggtcagga agcatgtggt tcatcctttg   1200
gaaatggtag taggaaacca tacagtcttt ggcattcga gctacataaa ggaactttgg   1260
ggtaagaaaa gaggtgggta aaagatggta taaaaagtgg actt                   1304
```

<210> 37
<211> 1080
<212> DNA

UNITED STATES PATENT AND TRADEMARK OFFICE
CERTIFICATE OF CORRECTION

| | |
|---|---|
| PATENT NO. | : 7,026,163 B1 |
| APPLICATION NO. | : 09/792695 |
| DATED | : April 11, 2006 |
| INVENTOR(S) | : Freimuth et al. |

It is certified that error appears in the above-identified patent and that said Letters Patent is hereby corrected as shown below:

<213> Homo sapiens

<400> 37
```
tatatgacct agcactggga ctattcacca agttttggtc ttctgacatc tcctctgtgc    60
acttccattt tattcccacc caccagtgag ggcactcagg ccatgtttcc tcagggctgg   120
ctgcaccagg gtttccctca aagtgttcct tctgatagtg accagacaga actccaggat   180
tgagcccagg ctggagttgc ctgaatggcc aggacagatg acagaaattt tgtttttaat   240
atagatataa cctaatattt ggacttatac tcaaggtatt atgatgttat agactgggag   300
actaggatgc actttccaga ataatgggga ttaaaacaat cctttgtac tcaagtcata    360
cgttttactt agtttattaa gctaccttat atcttactt ggaaagaata gttgggaaaa    420
tgggcattag acgtgatcct ttttaaaaaa tgaagtggtg acatactgtt aatcatcaca   480
gagattgttt gtactacatt gtatacattc acaatatgct ttcagagatt cttctggctg   540
ggactgaagg attgaagata gtatttgcac tcttgccatc caccttttaa ttttatttac   600
atcttgctca gagttccatg cagaagttta tggaggttcc ttccatcttt cttctataga   660
tttcatcaaa cctctcattc tgggcaacag tgaagtggtt tttccaatcc cccacagttc   720
ctagaaaaag gaaggccaga caggagtgtc actctgattg aaagatgtgg tgtccctgag   780
taaagtggtg tagtgcccat actgaatctg gcctgtccac ataacctgact cacccaactc   840
cccctcagt ggacacctgt ccatgagcag ctctcctata agaagcaggc ctaggggact    900
ctgtgcaggg ggatggactt ctaagtcagc tggacaactg acccaaggca gctagtggcc   960
tgcatgacct ggcccccacct gtagtgtatt tacctgatgg attactacat agacataaaa  1020
gaatgatgaa ctacagacac acaaccacat ggaggaatct caaaacatta tgttgagcaa  1080
``` --therefor.

Signed and Sealed this

Fourteenth Day of October, 2008

JON W. DUDAS
*Director of the United States Patent and Trademark Office*